United States Patent [19]

Marfat et al.

[11] Patent Number: 5,811,432
[45] Date of Patent: Sep. 22, 1998

[54] AZAOXINDOLE DERIVATIVES

[75] Inventors: Anthony Marfat, Mystic; Ralph P. Robinson, Gale Ferry, both of Conn.

[73] Assignee: Pfizer Inc, New York, N.Y.

[21] Appl. No.: 33,456

[22] Filed: Mar. 18, 1993

Related U.S. Application Data

[63] Continuation of Ser. No. 960,208, Oct. 13, 1992, abandoned, which is a continuation of Ser. No. 846,756, Mar. 5, 1992, abandoned, which is a continuation of Ser. No. 612,054, Nov. 9, 1990, abandoned.

[51] Int. Cl.$^6$ .......................... A01N 43/40; C07D 471/04
[52] U.S. Cl. ............................................ 514/300; 546/113
[58] Field of Search .............................. 546/113; 514/300

[56] References Cited

U.S. PATENT DOCUMENTS 5,182,289  1/1993  Ting et al. ............................... 514/278

*Primary Examiner*—Johann Richter
*Assistant Examiner*—Ebenezer Sackey
*Attorney, Agent, or Firm*—Peter C. Richardson; Paul H. Ginsburg; Garth Butterfield

[57] ABSTRACT

This invention relates to novel 4-, 5-, 6-, and 7-azaoxindole derivatives. The compounds are anti-inflammatory and analgesic agents and inhibitors of one or more of prostaglandin $H_2$ synthase, 5-lipoxygenase and interleukin-1 biosynthesis. They are useful in the treatment of chronic inflammatory diseases, allergy, psoriasis, various bone diseases, and immune dysfunctions such as systemic lupus erythematosis.

12 Claims, No Drawings

AZAOXINDOLE DERIVATIVES

This is a continuation of application Ser. No. 07/960,208, filed on Oct. 13, 1992 now abandoned, which is a continuation of application Ser. No. 07/846,756 filed on Mar. 5, 1992 now abandoned which is a continuation of U.S. Ser. No. 07/612,054 filed on Nov. 9, 1990 now abandoned, which is a continuation in part of International Appln. No. PCT/US90/00107 filed Jan. 5, 1990.

BACKGROUND OF THE INVENTION

This invention relates to azaoxindoles, more particularly, 4-,5-,6-, and 7-azaoxindole derivatives, pharmaceutical compositions comprising such compounds and methods of treatment with such compounds.

U.S. Pat. No. 4,569,942 discloses certain 2-oxindole-1-carboxamides of the formula

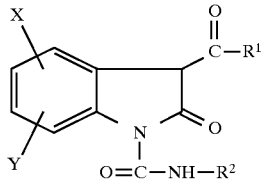

wherein, inter alia, X is H, fluoro, chloro, bromo, $(C_1-C_4)$ alkyl, $(C_3-C_7)$cycloalkyl, $(C_1-C_4)$alkoxy, $(C_1-C_4)$alkylthio, trifluoromethyl, $(C_1-C_4)$alkylsulfinyl, $(C_1-C_4)$ alkylsulfonyl, nitro, phenyl, $(C_2-C_4)$alkanoyl, benzoyl, thenoyl, $(C_1-C_4)$alkanamido, benzamido or N,N-dialkylsulfamoyl having 1 to 3 carbons in each of said alkyls; Y is, H, fluoro, chloro, bromo, $(C_1-C_4)$alkyl, $(C_3-C_7)$ cycloalkyl, $(C_1-C_4)$alkoxy, $(C_1-C_4)$alkylthio and trifluoro; $R^1$ is $(C_1-C_6)$alkyl, $(C_3-C_7)$cycloalkyl, $(C_4-C_7)$ cycloalkenyl, phenyl, substituted phenyl, phenylalkyl having 1 to 3 carbons in said alkyl, (substituted phenyl)alkyl having 1 to 3 carbons in said alkyl, (substituted phenoxy) alkyl having 1 to 3 carbons in said alkyl, (thiophenoxy)alkyl having 1 to 3 carbons in said alkyl, naphthyl, bicyclo[2.2.1] heptan-2-yl, bicyclo[2.2.1]hept-5-en-2-yl or —$(CH_2)_n$— Q—$R^o$; n is zero, 1 or 2; Q is a divalent radical derived from furan, thiophene, pyrrole, pyrazole, imidazole, thiazole, isothiazole, oxazole, isoxazole, 1,2,3-thiadiazole, 1,3,4-thiadiazole, 1,2,5-thiadiazole, tetrahydrofuran, tetrahydrothiophene, tetrahydropyran, tetrahydrothiopyran, pyridine, pyrimidine, pyrazine, benzo[b]furan and benzo[b] thiophene; $R^o$ is H or $(C_1-C_3)$alkyl; and $R^2$ is $(C_1-C_6)$alkyl, $(C_3-C_7)$cycloalkyl, benzyl, furyl, thienyl, pyridyl or

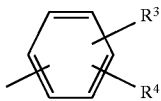

wherein $R^3$ and $R^4$ are each H, fluoro, chloro, $(C_1-C_4)$-alkyl, $(C_1-C_4)$alkoxy or trifluoromethyl.

That patent also discloses that said 2-oxindole-1-carboxamides are inhibitors of cyclooxygenase and lipoxygenase, possess analgesic activity in mammals and are useful in treatment of pain and alleviation of symptoms of chronic diseases such as inflammation and pain associated with rheumatoid arthritis and osteoarthritis.

U.S. Pat. No. 4,556,672 discloses certain 3-acyl substituted-2-oxindole-1-carboxamides of the formula

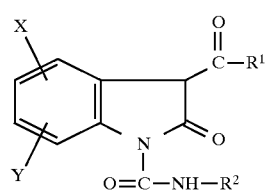

wherein X, Y and $R^1$ are as described above for the compounds of U.S. Pat. No. 4,569,942. The compounds of U.S. Pat. No. 4,556,672 are disclosed as having the same activity as the compounds of U.S. Pat. No. 4,569,942 discussed above.

U.S. patent application Ser. No. 181,131, filed Apr. 13, 1988 and assigned to the assignee hereof discloses the use of compounds of the formula

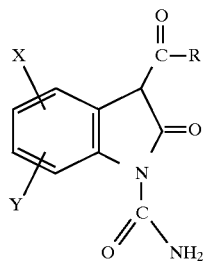

and the pharmaceutically-acceptable base salts thereof, wherein X is H, Cl or F, Y is H or Cl and R is benzyl or thienyl, to inhibit biosynthesis of interleukin-1 (IL-1) and to treat IL-1 mediated disorders and dysfunctions.

PCT patent application Ser. No. PCT/US88/03658, filed Oct. 18, 1988 and assigned to the assignee hereof, describes non-steroidal antiinflammatory agents of the formula

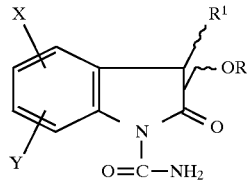

wherein each of X and Y is hydrogen, fluoro or chloro; $R^1$ is 2-thienyl or benzyl; R is alkanoyl of two to ten carbon atoms, cycloalkylcarbonyl of five to seven carbon atoms, phenylalkanoyl of seven to ten carbon atoms, chlorobenzoyl, methoxybenzoyl, thenoyl, omega-alkoxycarbonylalkanoyl, said alkoxy having one to three carbon atoms and said alkanoyl having three to five carbon atoms; alkoxycarbonyl of two to ten carbon atoms; phenoxycarbonyl; 1-(acyloxy) alkyl, said acyl having one to four carbon atoms and said alkyl having two to four carbon atoms; 1-(alkoxycarbonyloxy)alkyl said alkoxy having two to five carbon atoms and said alkyl having one to four carbon atoms; alkyl of one to three carbon atoms; alkylsulfonyl of one to three carbon atoms; methylphenylsulfonyl or dialkylphosphonate, each said alkyl of one to three carbon atoms.

The compounds of the present invention are anti-inflammatory and analgesic agents and inhibitors of one or more of prostaglandin $H_2$ synthase, 5-lipoxygenase and interleuken-1 biosynthesis. Prostaglandin $H_2$ synthase and 5-lipoxygenase catalyze the syntheses in vivo of classes of compounds known as, respectively, prostaglandins and leukotrienes, both of which are mediators in several inflammatory diseases. For example, prostaglandin $H_2$ synthase is known to be involved with, among other disease states, the pathogenesis of arthritic joints in mammals. Leukotrienes are known mediators of, among other diseases, asthma, arthritis, psoriasis, ulcers, stroke myocardial infarction and irritable bowel disease.

The ability of the compounds of this invention to inhibit prostaglandin $H_2$ synthase and 5-lipoxygenase, and thus inhibit the synthesis of prostaglandins and leukotrienes, make them useful in the prevention and treatment of both prostaglandin mediated diseases and leukotriene mediated diseases.

The ability of the compounds of formula I to inhibit IL-1 biosynthesis makes them useful in treating IL-1 mediated disorders and immune dysfunctions in a mammal. IL-1 mediated disorders include, but are not limited to bone and connective tissue metabolism disorders such as osteoporosis, peridontal disease and tissue scarring. IL-1 mediated immune dysfunctions include, but are not limited to, allergy, psoriasis, and systemic lupus erythematosis.

The analgesic activity of the compounds of formula I makes them useful for administration to mammals for the control of pain, e.g., post-operative pain and the pain of trauma. Their analgesic activity also renders them useful for chronic administration to mammals for the alleviation of the symptoms of chronic diseases, such as the inflammation of rheumatoid arthritis, and the pain associated with osteoarthritis and other musculo-skeletal disorders.

SUMMARY OF THE INVENTION

The present invention relates to compounds of the formula

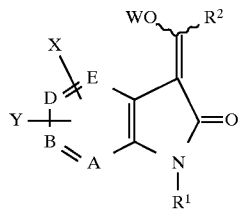

I wherein one of A, B, D and E is N and the others are CH; X and Y are independently selected from hydrogen, $OR^3$, hydroxy, $(C_1-C_6)$ alkyl, $CF_3$, $COR^3$, halogen (e.g., fluoro, chloro, bromo or iodo), $COOR^3$, $CONR^3R^3$, CN, $NO_2$, $SR^3$, $SOR^3$, $SO_2R^3$ and $SO_2NR^3R^3$; $R^1$ is $(C_1-C_6)$ alkyl or $CONHR^4$; $R^2$ is $(C_1-C_8)$ alkyl (preferably $(C_3-C_8)$ cycloalkyl), $(CH_2)_nR^5$ wherein n is 0 or 1, or $NHR^6$; $R^3$ is $(C_1-C_6)$ alkyl, phenyl, benzyl, allyl or hydrogen, wherein said phenyl and the phenyl moiety of said benzyl may optionally be substituted with one or more substituents independently selected from fluoro, chloro, bromo, iodo, hydroxy, $(C_1-C_3)$alkyl, $(C_1-C_3)$alkoxy and $CF_3$; $R^4$ is hydrogen, $(C_1-C_6)$alkyl, $(C_2-C_6)$hydroxyalkyl, $(C_3-C_8)$ cycloalkyl, $COR^3$ wherein $R^3$ is as defined above, phenyl, substituted phenyl, heteroaryl or substituted heteroaryl, wherein the heteroaryl moiety of each of said heteroaryl and substituted heteroaryl groups is selected from thiophene and furan, and wherein each of said substituted phenyl and substituted heteroaryl groups is substituted with one or two substituents independently selected from fluoro, chloro, bromo, iodo, hydroxy, $(C_1-C_3)$ alkyl, $(C_1-C_3)$ alkoxy and $CF_3$; $R^5$ is $(C_3-C_8)$ cycloalkyl, hydrogen, phenyl, substituted phenyl, heteroaryl and substituted heteroaryl, wherein the heteroaryl moiety of each of said heteroaryl and substituted heteroaryl groups is selected from thiophene and furan, and each of said substituted phenyl and substituted heteroaryl groups is substituted with one or two substituents independently selected from fluoro, chloro, bromo, iodo, hydroxy, $(C_1-C_3)$ alkyl, $(C_1-C_3)$ alkoxy and trifluoromethyl; $R^6$ is phenyl, thiophene or furan, wherein said phenyl, thiophene and furan may be optionally substituted with one or more substituents independently selected from fluoro, chloro, bromo, iodo, hydroxy, $(C_1-C_6)$ alkyl, $(C_1-C_3)$ alkoxy and trifluoromethyl; and W is hydrogen, $(C_2-C_{10})$ alkanoyl, $(C_5-C_7)$ cycloalkylcarbonyl, $(C_7-C_{10})$ phenylalkanoyl, chlorobenzoyl, thenoyl, omega-$(C_2-C_4)$ alkoxycarbonyl$(C_3-C_5)$alkanoyl, $(C_2-C_{10})$alkoxycarbonyl, phenoxycarbonyl, 1-[$(C_1-C_4)$acyloxy]-$(C_2-C_4)$alkyl, 1-[$(C_2-C_5)$alkoxy-carbonyloxy]-$(C_1-C_4)$alkyl, $(C_1-C_3)$ alkylsulfonyl, $(C_1-C_3)$alkyl, methylphenylsulfonyl and di-$(C_1-C_3)$alkyl phosphonate; with the proviso that (a) when E is nitrogen, then at least one of X and Y is other than hydrogen; (b) when either $R^2$ is $NHR^6$ or $R^1$ is $(C_1-C_6)$alkyl, then W is hydrogen.

The present invention also relates to pharmaceutically acceptable acid or base addition salts of the compounds of formula I. Examples of suitable acid addition salts are those of acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic (e.g. methanesulfonic and benzenesulfonic), and related acids. Preferably, the acid addition salt is of phosphoric acid. Typical base addition salts of the compounds of formula I which can be prepared are salts of primary, secondary and tertiary amines, and those of alkali and alkaline earth metals. Especially valuable are the ethanolamine, diethanolamine and triethanolamine salts.

A preferred embodiment of the invention relates to compounds of the formula I wherein B or E is nitrogen, at least one of X and Y is chloro, $R^2$ is $(CH_2)_n R^5$, n is O, $R^5$ is unsubstituted heteroaryl, $R^1$ is $CONHR^4$ and $R^4$ is hydrogen or $(C_1-C_6)$alkyl.

Specific preferred compounds of the formula I are:
5-Chloro-3-(2-thenoyl)-4-azaoxindole-1-N-t-butylcarboxamide;
5-Chloro-3-(2-furoyl)-4-azaoxindole-1-N-t-butylcarboxamide;
6-Chloro-3-(2-thenoyl)-4-azaoxindole-1-carboxamide;
5-Chloro-3-(2-thenoyl)-6-azaoxindole-1-N-t-butylcarboxamide;
5,6-Dichloro-3-(2-thenoyl)-4-azaoxindole-1-N-t-butylcarboxamide;
5-Chloro-3-(4-methyl-2-thenoyl)-4-azaoxindole-1-N-t-butylcarboxamide;
5-Chloro-3-(4-chloro-2-thenoyl)-4-azaoxindole-1-N-t-butylcarboxamide;
5-Chloro-3-(3-furoyl)-4-azaoxindole-1-N-t-butylcarboxamide; and
5-Chloro-3-(2-thenoyl)-4-azaoxindole-1-N-phenyl carboxamide.

Other specific compounds of the formula I are:
5-Chloro-3-(3-thenoyl)-4-azaoxindole-1-N-t-butyl carboxamide;
3-(2-Furoyl)-5-trifluoromethyl-4-azaoxindole-1-N-t-butylcarboxamide;
3-(2-Thenoyl)-6-trifluoromethyl-4-azaoxindole-1-carboxamide;
6-Chloro-3-(3-furoyl)-5-azaoxindole-1-N-t-butylcarboxamide;
5-Acetyl-3-(2-thenoyl)-4-azaoxindole-1-N-t-butyl carboxamide;

5-Cyano-3-(2-thenoyl)-4-azaoxindole-1-N-t-butylcarboxamide;

3-(2-furoyl)-5-trifluoromethyl-6-azaoxindole-1-N-cyclohexylcarboxamide; and

5-Chloro-3-phenylacetyl-6-azaoxindole-1-N-t-butylcarboxamide.

The present invention also relates to compounds of the formula

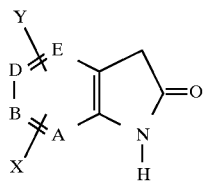

wherein A, B, D, E, X and Y are as defined for formula I. These compounds are intermediates in the synthesis of compounds of the formula I.

The present invention also relates to a pharmaceutical composition for preventing or treating a condition selected from the group consisting of chronic inflammatory diseases such as asthma, psoriasis, rheumatoid arthritis, and osteoarthritis, and immune dysfunctions such as systemic lupus erythematosis, in a mammal, including a human, comprising an amount of a compound of the formula I, or a pharmaceutically acceptable salt thereof, effective in preventing or alleviating such condition, and a pharmaceutically acceptable carrier.

The present invention also relates to a pharmaceutical composition for preventing or treating pain in a mammal, including a human, comprising an amount of a compound of the formula I, or a pharmaceutically acceptable salt thereof, effective in preventing or alleviating pain, and a pharmaceutically acceptable carrier.

The present invention also relates to a method of preventing or treating a condition selected from the group consisting of chronic inflammatory diseases such as asthma, psoriasis, rheumatoid arthritis, and osteoarthritis, and immune dysfunctions such as systemic lupus erythematosis, in a mammal, including a human, comprising administering to said mammal an amount of a compound of the formula I, or a pharmaceutically acceptable salt thereof, effective in preventing or alleviating said condition.

The present invention also relates to a method of preventing or treating pain in a mammal, including a human, comprising administering to said mammal an amount of a compound of the formula I, or a pharmaceutically acceptable salt thereof, effective in preventing or alleviating pain.

The present invention also relates to a pharmaceutical composition for inhibiting 5-lipoxygenase or interleukin-1 synthesis in a mammal, including a human, comprising a 5-lipoxygenase inhibiting or interleuken-1 synthesis inhibiting amount of a compound of the formula I, or a pharmaceutically acceptable salt thereof, and a pharmaceutically acceptable carrier.

The present invention also relates to a method of inhibiting 5-lipoxygenase or interleukin-1 synthesis in a mammal, including a human, comprising administering to said mammal a 5-lipoxygenase inhibiting or interleukin-1 synthesis inhibiting amount of a compound of the formula I, or a pharmaceutically acceptable salt thereof.

The present invention also relates to a pharmaceutical composition for inhibiting prostaglandin $H_2$ synthase synthesis in a mammal, including a human, comprising an amount of a compound of the formula I, or a pharmaceutically acceptable salt thereof, effective in inhibiting such synthesis, and a pharmaceutically acceptable carrier.

The present invention also relates to a method of inhibiting prostaglandin $H_2$ synthase synthesis in a mammal, including a human, comprising administering to said mammal an amount of a compound of the formula I, or a pharmaceutically acceptable salt thereof, effective in inhibiting such synthesis.

The term "alkyl", as used herein, refers to saturated monovalent hydrocarbon radicals having straight, branched or cyclic moieties or combinations thereof.

Compounds of the formula I wherein W is other than hydrogen are prodrugs of compounds of the formula I wherein W is hydrogen. The term "prodrug" refers to compounds that are drug precursors that, following administration to and absorption by a mammal, release the drug in vivo via a metabolic process.

The compounds of formula I exist in several tautomeric forms, due to the presence of the carbonyl carbon at position 2 on the azaoxindole ring and the acyl carbon attached to the carbon at position 3 of the ring. Such compounds also exist as geometric isomers of the tautomeric structure in which a double bond exists. This invention relates to all tautomeric forms and geometric isomers of the compounds of Formula I.

DETAILED DESCRIPTION OF THE INVENTION

Compounds of the formula I wherein W is hydrogen may be prepared as shown in schemes 1–5 below.

Except where otherwise noted, A, B, D, E, X, Y, $R^1$, $R^2$, $R^3$, $R^4$, $R^5$ and $R^6$ in the reaction schemes and discussion that follow are defined as above.

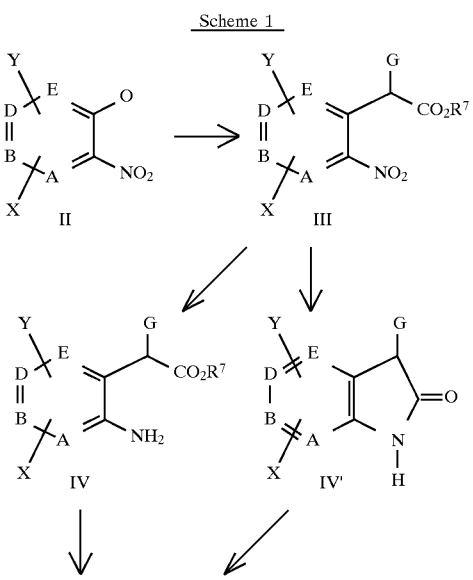

-continued
Scheme 1
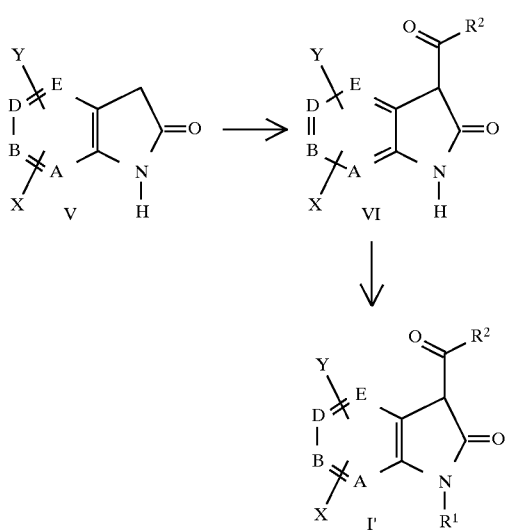
Scheme 2
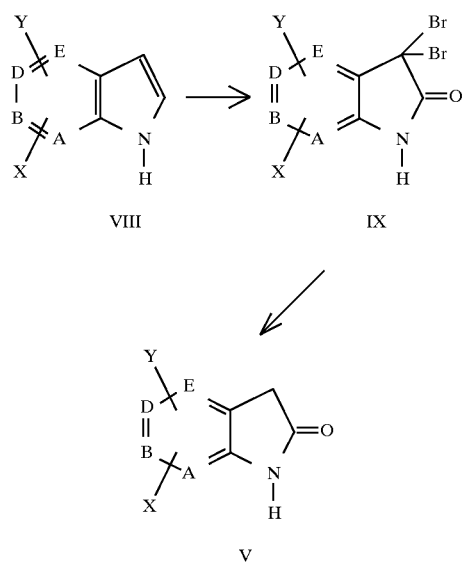
Scheme 3
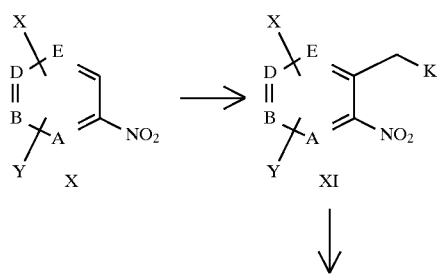
-continued
Scheme 3
Scheme 4
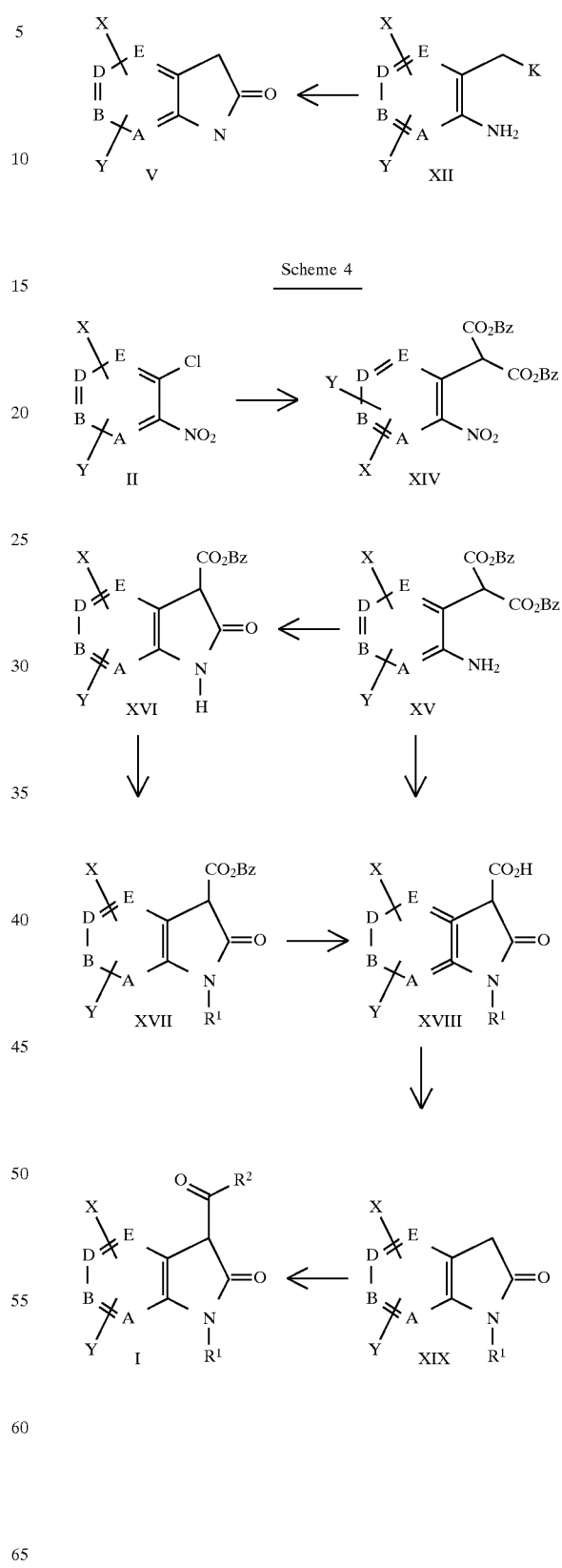

Scheme 5

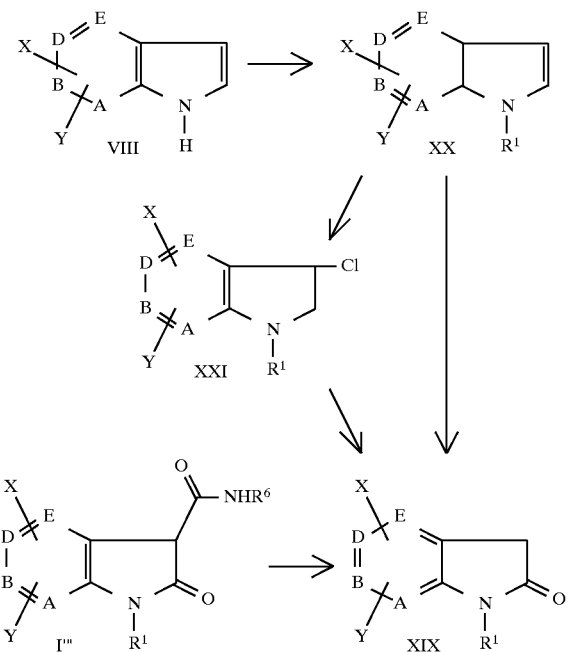

Referring to scheme I, compounds of the formula I' may be obtained as follows. A compound of the formula II, wherein Q is halogen, is reacted with a dialkyl malonate ester of the formula $R^7O_2CCH_2CO_2R^8$, wherein $R^7$ and $R^8$ are the same or different and selected from ($C_1$–$C_6$) alkyl and benzyl, or with a cyanoacetate of the formula $NCCH_2CO_2R^7$, in an aprotic solvent such as dimethylformamide or 1,2-dimethoxyethane, at a temperature from about −30° to about 50° C. The preferred solvent is 1,2-dimethoxyethane and the preferred temperature is 25° C. A nitro compound of formula III, wherein G is $CO_2R^8$ or CN and $R^7$ and $R^8$ are as defined above, is obtained.

The compound of formula III is then reduced to produce the corresponding amino compound of formula IV, wherein $R^7$ and G are as defined above, or an azaoxindole of the formula IV', wherein G is as defined above. (One or both products may be formed). This reaction is typically carried out under a hydrogen atmosphere in a suitable solvent with a metal catalyst at a temperature from about 0° C. to about 70° C., preferably at ambient temperature (about 20° C.). Suitable solvents include methanol, ethanol, propanol, ethyl acetate, and dimethylformamide. Ethanol is the preferred solvent. The preferred catalyst is Raney nickel. The hydrogen pressure of the reaction should be maintained between about 1 atmosphere and about 5 atmospheres, preferably at about 3 atmospheres. Removal of the catalyst by filtration and removal of the solvent yields one or both of a compound of the formula IV and a compound of the formula IV'. Alternatively, the nitro compound of formula III can be reduced using a metal such as zinc, iron or tin, and an acid such as aqueous hydrochloric acid or acetic acid. This reaction also produces one or both of a compound of the formula IV and a compound of the formula IV', wherein $R^7$ and G are as defined above. Temperatures from about 0° to about 120° C. are suitable, with room temperature being preferred as a matter of convenience.

Azaoxindoles of formula V may be prepared from the corresponding compounds of formula IV or IV', wherein $R^7$ and G are as defined above, produced in the above reaction by isolating such compounds and reacting them with dilute hydrochloric acid, hydrobromic acid or sulfuric acid, at a temperature from about 50° C. to about the reflux temperature of the reaction mixture, preferably at the reflux temperature.

With the azaoxindole nucleus of formula V in hand, azaoxindole-1-carboxamides of the formula I may be prepared as follows.

The first step involves attachment of the 3-acyl substituent. This acylation reaction may be carried out by reacting a compound of the formula V with a derivative of an appropriate acid of the formula $R^2COOH$ in a lower alkanol solvent (e.g., ethanol) in the presence of an alkali metal salt of the lower alkanol solvent (e.g., sodium ethoxide) using standard procedures. Typical derivatives of the acid of the formula $R^2COOH$ which may be used include acid chlorides, acid anhydrides of the formula $R^2$ $COOCOR^2$, and alkyl esters of the formula $R^2COO$-($C_1$ to $C_6$ alkyl).

An excess of the derivative of the acid may be used and the alkoxide salt may be present in an amount from one to seven molar equivalents based on the derivative. It is preferred to use 5 equivalents of alkoxide salt with 2 equivalents of a simple alkyl ester or 7 equivalents of alkoxide salt with 2 equivalents of acid chloride or anhydride.

The reaction between the derivative of the acid of the formula $R^2COOH$ and the compound of formula V is usually started at a temperature from about 0° to about 25° C. The reaction mixture is then typically heated at a temperature in the range from about 50° to about 130° C., preferably at about 80° C., to complete the reaction. Under these circumstances, reaction times of a few hours, e.g. two hours, up to a few days, e.g., two days, are commonly used. The reaction mixture is then cooled, diluted with an excess of water, and acidified.

The acylated product having formula VI can then be recovered by filtration or by the standard procedure of solvent extraction.

The compound of formula VI so formed may be reacted with chlorosulfonyl isocyanate to prepare a compound having a formula identical to formula I except that $R^1$ is $CONHSO_2$ Cl (hereinafter referred to as formula VII). The reaction is conducted in a reaction-inert solvent, i.e. a solvent which does not react with the chlorosulfonyl isocyanate or the N-chlorosulfonyl-2-oxindole-1-carboxamide product of formula VII. Representative solvents are dialkyl ethers such as diethyl ether; cyclic ethers such as dioxane and tetrahydrofuran; aromatic hydrocarbons such as benzene, xylene and toluene; chlorinated hydrocarbons such as methylene chloride and chloroform; acetonitrile; and mixtures thereof.

The reaction is generally conducted at temperatures ranging from ambient temperature to the reflux temperature of the solvent used. In general, temperatures of from about 25° to about 110° C. are favored. Temperatures below 20° C., e.g. down to −70° C., can be used if desired. However, temperatures below 0° C. are avoided, if practical, for reasons of economy because they result in a lower yield.

The compound of formula VI and chlorosulfonyl isocyanate are generally reacted in molar proportions ranging from equimolar to 30% excess of chlorosulfonyl isocyanate, i.e., 1:1 to 1:1.3. Larger excesses of chlorosulfonyl isocyanate appear to afford no advantages and are not used for reasons of economy.

The chlorosulfonyl derivatives of formula VII thus produced can be isolated, if desired, or can be converted directly via hydrolysis in the same reaction vessel without isolation to a compound of the formula I wherein $R^1$ is $CONH_2$. Isolation of the intermediate chlorosulfonyl compounds of formula VII is achieved by procedures known to those skilled in the art, e.g., by filtration or by evaporation of the solvent.

The hydrolysis of the chlorosulfonyl derivative of formula VII is carried out by treating such compound, with or without isolation thereof, with water (preferably ice water), aqueous acid or aqueous base. Water alone or aqueous acid are generally favored, even in instances wherein the hydrolysis step involves a two-phase system. While the rate of hydrolysis is sufficiently rapid as to overcome solubility problems, the use of water alone is more economical from the standpoint of large scale reactions than are the other hydrolysis methods.

The amount of acid is not critical to the hydrolysis step. It can range from less than equimolar quantities to greater than equimolar quantities. Also not critical is the concentration of the acid use. In general, when aqueous acid is used for the hydrolysis step, from about 0.1–3.0 moles of acid per mole of compound of formula VII are used. Acid concentrations of from about 1 to 6 molar are generally used for ease in handling. The use of aqueous acid is often resorted to when the intermediate of formula VII is isolated and a single-phase hydrolysis mixture is desired. Representative acids are hydrochloric, sulfuric, nitric, phosphoric, acetic, formic, citric and benzoic acids.

It is often preferable to carry out the hydrolysis simply by stirring the N-chlorosulfonyl carboxamides in a solution of DMSO left open to the air at about room temperature. Higher temperatures (greater than 50° C.) can lead to subsequent hydrolysis of the product. Lower temperatures down to the freezing point of DMSO can be used but result in lower reaction rates. This reaction can be easily followed by $^1H$ NMR using DMSO-$d_6$ as the solvent. On completion of the reaction, the mixture is poured into an excess of water and the crude product is isolated by filtration. Solvents other than DMSO may also be used. Examples of suitable solvents include chloroform and dimethylformamide.

Compounds of the formula I, wherein W is hydrogen, $R^1$ is $CONHR^4$ and $R^4$ is other than hydrogen, may be prepared according to scheme 1 by reacting a compound of the formula VI or a compound of the formula VII with an isocyanate of the formula $R^4$—N=C=O. Most commonly, the reaction is carried out by contacting substantially equimolar quantities of the reactants in an inert solvent at a temperature in the range from about 25° to about 150° C., preferably from about 80° to about 130° C. In this context, an inert solvent is one which will dissolve at least one of the reactants, and which does not adversely interact with either of the reactants or the product. Typical solvents which can be used include aliphatic hydrocarbons, such as octane, nonane, decane and decalin; aromatic hydrocarbons, such as benzene, chlorobenzene, toluene, xylenes and tetralin; chlorinated hydrocarbons, such as 1,2-dichloroethane; ethers, such as tetrahydrofuran, dioxane, 1,2-di-methoxyethane and di(2-methoxyethyl) ether; and polar, aprotic solvents such as N,N-dimethylformamide, N,N-dimethylacetamide, N-methylpyrrolidone and sulfoxide. The reaction time varies according to the reaction temperature, but at a temperature from 100° to 130° C. reaction times of a few hours, e.g., 5 to 10 hours, are commonly used.

When a relatively non-polar reaction solvent is used for the reaction of a compound of formula VI with an isocyanate of formula $R^4$—N=C=O, the product is usually out of solution at the end of the reaction when the reaction mixture is cooled to room temperature. Under these circumstances, the product is usually recovered by filtration. However, if relatively polar solvents are used and the product is not out of solution at the end of the reaction, the product can be recovered by solvent evaporation. Alternatively, in the case of water-miscible solvents, dilution of the reaction medium with water causes the product to precipitate, and again it can be recovered by filtration. The reaction product can be purified by standard methods., e.g. recrystallization.

The reaction between a compound of formula VI and an isocyanate of formula $R^4$—N=C=O can be speeded up by the addition of a base, such as a tertiary amine, e.g. trimethylamine, triethylamine, tributylamine, N-methylpiperidine, N-methylmorpholine or N,N-dimethylaniline. From about one to four equivalents of the basic agent are usually added. This permits the use of reaction temperatures from about 20° to about 100° C. At the end of the reaction, the reaction medium must be neutralized (or made acidic), and then the product may be isolated as described earlier.

Preferred conditions used for the preparation of compounds of the formula IA wherein $R^1$ is $COHNR^4$ are: solvent—DMSO; temperature—80° C. to 100° C.; base—triethylamine (2 equivalents); isocyanate—1.5 equivalents; time—3 to 6 hours.

The isocyanates of the formula $R^4$—N=C=O can be prepared by standard procedures. (Sandler and Daro, "Organic Functional Group Preparations", Part I, Second Edition, Academic Press, Inc., New York, N.Y., Chapter 12, pp. 364–369 (1983)). A particularly useful method involves reaction of the appropriate amine of formula $R^4$—$NH_2$ with phosgene:

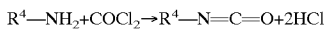

Variations of the method illustrated in scheme 1 for the preparation of compounds of the formula V wherein X and Y are both hydrogen (i.e., unsubstituted 4 and 6-azaoxindoles) have been described in the literature. (See Finch et al., *Journal of Organic Chemistry*, 37, 51 (1972); Daisley and Hanbali, *Synthetic Communications*, 11, 743 (1981), Parrick et al., *Journal of the Chemical Society*, 1531 (1974)).

Schemes 2 and 3 illustrate alternate methods of preparing azaoxindoles of formula V.

Referring to scheme 2, an azaindole of the formula VIII is reacted with 3 equivalents of bromine to produce the dibrominated compound of formula IX. Examples of suitable reagents are bromine, pyridinium bromide perbromide and N-bromosuccinimide. The reaction is carried out in a polar, inert solvent such as t-butyl alcohol/water or t-butyl alcohol, preferably t-butyl alcohol/water, having a pH between 1 and 7. Suitable reaction temperatures are from about 0° to about 50° C., with 25° C. being preferred. The compound of the formula IX so formed is then reduced by reaction with hydrogen gas to yield an azaoxindole of the formula V. The reduction is typically carried out at a temperature from about 25° to about 50° C. and a pressure from about 1 to about 5 atmospheres, in the presence of a 10% palladium on carbon catalyst. Twenty-five degrees Centigrade is the preferred temperature and 3 atmospheres is the preferred pressure.

Azaoxindoles of the formula V wherein D is nitrogen (5-axaoxindoles) may be produced according to scheme 2 by a variation of the foregoing procedure. Compounds of the formula VIII wherein D is nitrogen are reacted with 4 rather than three equivalents of bromine to yield, upon slow adjustment of the pH of the mixture to about 6.5 to about 7, compounds of the formula IX wherein X is bromine and is attached to the carbon at the "7" position of the azaoxindole ring. Subsequent hydrogenolysis of the carbon-bromine bonds yields compounds of the formula V wherein D is nitrogen. The latter reaction is generally carried out using 10% palladium on carbon at a pressure from about 1 to about 5 atm, preferably 3 atm.

The synthesis of compounds of the formula V wherein A is nitrogen, according to scheme 2, is exemplified in the literature. Marfat and Carta, *Tetrahydron Letters*, 28, 4027 (1987).

Scheme 3 illustrates another route useful for making compounds of the formula V (and thus of formula I). Referring to scheme 3, a compound of the formula X is reacted with 2-(4-chlorophenoxy)acetonitrile to produce a compound of the formula XI, wherein K ix CN. The reaction is typically carried out in the presence of a strong base in an appropriate solvent. (See Makosza, et al. (*Liebigs Ann. Chem.*, 1988, 203)). Suitable bases include tertiary sodium or potassium alkoxides. The preferred base is potassium t-butoxide. Suitable solvents include tetrahydrofuran, diethyl ether, and dimethylformamide. The preferred solvent is tetrahydrofuran. The reaction is conducted at a temperature of about –78° C. to about 25° C., preferably –10° C. The compound of the formula XI so produced is purified by neutralization of the reaction mixture using a mineral acid, preferably dilute hydrochloric acid, and standard extractive isolation using ethyl acetate, diethyl ether or methylene chloride, preferably diethyl ether. The organic residue from the extraction is then reduced to form a compound of the formula XII wherein K is CN. This reaction is typically carried out under a hydrogen atmosphere in a suitable solvent with a metal catalyst at a temperature from about 0° C. to about 70° C., preferably at ambient temperature (about 20° C.). Suitable solvents include methanol, ethanol, propanol, ethyl acetate, and dimethylformamide. Ethanol is the preferred solvent. The preferred catalyst is Raney nickel. The hydrogen pressure of the reaction should be maintained between about 1 atmosphere and about 5 atmospheres, preferably at about 3 atmospheres. Removal of the catalyst by filtration and removal of the solvent yields the product of formula XII.

The compound of formula XII so formed is then cyclized to the azaoxindole of formula V by hydrolysis in aqueous mineral acid. Examples of acceptable acids are aqueous sulfuric, hydrochloric, and hydrobromic acids. Reaction temperatures from about 25° to about 150° C. are suitable, with 150° C. being preferred.

The following procedure is a variant of the procedure illustrated in Scheme 3. A compound of the formula X is reacted with t-butyl(phenylthio)acetate in the presence of a strong base in an appropriate solvent (see Makosza and Winiarski, *J. Org. Chem.*, 49, (1984)). Suitable bases include sodium hydride and sodium hydroxide. The preferred base is sodium hydroxide. Suitable solvents include dimethylsulfoxide, liquid ammonia and pyridine. Dimethyl sulfoxide is the preferred solvent. The reaction is conducted at a temperature of about –78° to about 50° C., preferably at about 25° C. This reaction produces a compound of formula XI, wherein K is $CO_2tBu$, which is then purified as described above for compounds of formula XI wherein K is CN. The compound of formula XI, wherein K ix $CO_2tBu$, is then reduced to form a compound of the formula XII, wherein K is $CO_2tBu$. This reduction may be carried out by catalytic hydrogenation as described above for compounds of the formula XI wherein K is CN, or by reaction of the compound of formula XI wherein K is $CO_2tBu$ with a metal such as zinc, iron or tin in an acid such as aqueous hydrochloric acid or acetic acid. After isolation of the compound of the formula XII wherein K=$CO_2tBu$, it is cyclized to the corresponding azaoxindole of formula V by treating it with an acid in an inert solvent. Examples of acceptable acids are hydrochloric, trifluoroacetic and p-toluenesulfonic acids. Suitable solvents include methylene chloride, benzene and toluene. The preferred solvent is benzene. Reaction temperatures from about 25° to about 150° C. are acceptable, with 80° C. being preferred. In some cases, e.g. where reduction of the compound of the formula XI wherein K is $CO_2t$-Bu is carried out using a metal in an acid, cyclization of the compound of formula XII wherein K is $CO_2tBu$ can be achieved in situ. For in situ cyclization, 100° C. is the preferred temperature and acetic acid is the preferred acid.

The synthesis of certain compounds of the formula V wherein one of X and Y is methyl and the other is hydrogen is described by Daisley et al., *Synthetic Communictions*, 5 (1), 53–57 (1975).

Compounds of the formula I" wherein $R^1$ is $CONHR^4$ and W is hydrogen may also be prepared by the procedure illustrated in scheme 4. This procedure is a variation of the procedure of scheme 1 that involves acylating the "3" position of the azaoxindole nucleus prior to adding the $R^1$ substituent at the "1" position. To carry out this procedure, a compound of the formula II is reacted with an ester of the formula $CH_2(CO_2Bz)_2$, wherein Bz is benzyl, in an aprotic solvent such as 1,2-dimethoxyethane or N,N-dimethylformamide, in the presence of a base such as sodium hydride, and at a temperature from about –30° to about 50° C. This reaction produces a compound of the formula XIV, which is then converted into the corresponding amine of formula XV and azaoxindole of formula XVI according to the procedure of scheme 1 described above for forming azaoxindoles of formula V from esters of formula III. The azaoxindole of formula XVI is then substituted at the "1" position to form a azaoxindole of formula XVII, wherein $R^1$ is $CONHR^4$, by reacting it with an isocyanate of the formula $R^4$—N=C=O according to the procedure of scheme 1 described above for forming compounds of formula I from compounds of formula VI.

Reduction of the ester of formula XVII with hydrogen yields the corresponding carboxylic acid of the formula XVIII. This reaction is typically carried out at a pressure of about 1 to about 5 atmospheres, a temperature from about 25° to about 50° C., and in the presence of a 10% palladium on carbon catalyst. The acid of formula XVIII is then heated at a temperature from about 50° to about 200° C. to produce a compound of formula XIX, wherein the "3" position of the azaoxindole nucleus is unsubstituted.

The compound of formula XIX so formed is then re-acylated at the "3" position by reacting it with an acid chloride or anhydride of the formula $R^2COOCOR^2$ to form a compound of formula I. This reaction is typically carried out in a polar, aprotic solvent such as N,N-dimethylformamide, N,N-dimethylacetamide, N-methylpyrrolidone, dimethyl sulfoxide or methylene chloride, in the presence of a base such as triethylamine or 4-dimethylaminopyridine. N,N-dimethylformamide is the preferred solvent. During the the slow addition of the acid chloride or anhydride to the solution containing the compound of the formula XIX, the solvent and the base, the reaction mixture is typically cooled to about 0° C. It is then permitted to warm to about 25° C. and the reaction is continued at that temperature. Reaction times of about 30 minutes to about two hours are common. At the end of the reaction, the reaction mixture is acidified and the product is recovered, for example, by filtration. The recovered product can be washed, dried and further purified by standard methods such as recrystallization.

The following method is preferred for the preparation of compounds of the formula I wherein $R^2$ is $NHR^6$ from compounds of the formula XIX. A compound of the formula XIX is reacted with a compound of the formula $R^6NCO$. This reaction is typically carried out in a reaction-inert solvent, preferably a polar, aprotic solvent such as dimethylformamide, diethylformamide, N-methyl-2-pyrrolidone or dimethylsulfoxide. Further, it is preferred that the reaction be carried out in the presence of a base. Such bases include alkali and alkaline earth metal hydrides and tertiary organic amines. The preferred base is sodium hydride.

In practice, the isocyanate is added to the oxindole derivative and base in the appropriate solvent. It is preferable to employ about one molar equivalent of the isocyanate and base, with best results achieved by using an excess of as much as 50% of each. It is preferred that the reagents be combined in the cold, generally from about −10° to about 0° C., and that the reaction mixture be allowed to warm to room temperature. At a temperature from about room temperature to about 45° C., the reaction proceeds to completion in about a few minutes to about 18 hours depending on the reactivity of the isocyanate. Upon completion of the reaction, the product is isolated by adding the mixture to ice/water and treating with sufficient acid to provide a pH of from about 2 to about 5. The product can be filtered or extracted with a water immiscible solvent.

Scheme 5 illustrates the synthesis of compounds of the formula I''' wherein $R^1$ is $(C_1-C_6)$alkyl, starting with an azaindole nucleus of the formula VIII. An azaindole of the formula VIII is reacted with a compound of the formula $R^{10}Br$ or $R^{10}I$, wherein $R^{10}$ is $(C_1-C_6)$alkyl, to provide an N-substituted azaindole of the formula XX. This reaction is typically carried out in a reaction inert solvent in the presence of a base. Suitable bases include sodium or potassium hydroxide and sodium or potassium hydride. When using a hydroxide as a base, suitable solvents include acetone and dimethylsulfoxide, acetone being preferred. When using a hydride as a base, suitable solvents include dimethylsulfoxide and N,N-dimethylformamide. The reaction is generally carried out at a temperature from about 0° to about 150° C. The preferred temperature is about 25° C.

The following two methods may be used to prepare N-substituted azaoxindoles of the formula XIX, wherein $R^1$ is $(C_1-C_6)$alkyl, from azaindoles of the formula XX. The first method is analogous to that illustrated in scheme 2 for preparing N-substituted azaoxindoles of the formula V from azaindoles of the formula VIII, and proceeds via formation of an intermediate dibromoazaoxindole similar to that of formula IX, except that the nitrogen at the "1" position is substituted with $(C_1-C_6)$ alkyl.

The second method involves treatment of a compound of the formula XX with N-chlorosuccinimide to provide a 3-chloro azaindole of the formula XXI. This reaction is generally conducted in a reaction inert solvent such as methylene chloride, chloroform or t-butanol. Methylene chloride is the preferred solvent. Suitable temperatures range from about 0° to about 80° C.

Conversion of the 3-chloroazaindole of formula XXI to an azaoxindole of formula XIX is accomplished by reacting it with a strong acid, e.g. phosphoric, sulfuric or perchloric acid, using glacial acetic acid as the solvent. Suitable temperatures range from about 25° C. to about 120° C., with the preferred temperature being about 60° C. The preferred acid is phosphoric acid. Reaction times may vary from about 1 hour to about 7 days, depending on the substrate and temperature used.

Derivativization of the azaoxindoles of the formula XIX, wherein $R^1$ is $(C_1-C_6)$alkyl, to compounds of the formula I, wherein $R^1$ is $(C_1-C_6)$alkyl, may be carried out according to the method described above in the discussion of scheme 4 for preparing compounds of the formula I from compounds of the formula XIX.

Compounds of the formula I, wherein W is other than hydrogen, i.e. the prodrugs of the compounds wherein W is hydrogen, may be prepared by the following two methods, starting with the appropriate 3-acyl-3-azaoxindole-1-carboxamide (or N-substituted carboxamide). The first method involves treating a solution of the appropriate 3-acyl-azaoxindole-1-carboxamide (or N-substituted carboxamide) and an equimolar amount of triethylamine in a reaction-inert solvent such as chlorform or tetrahydrofuran, with a slight excess of the requisite acid chloride, chloroformate, oxonium salt or alkylating agent, at a temperature from about −10° to about 10° C., preferably about 0° C. The reaction is allowed to warm to room temperature and remain at that temperature for about 2–3 hours. If the starting oxindole is not completely reacted, the mixture is cooled again, additional acylating or alkylating agent and a proportional amount of triethylamine are added, and the process is repeated until all the starting oxindole has been consumed. The product is isolated from the reaction solvent after it has been washed with 1N hydrochloric acid and extracted with a saturated sodium bicarbonate solution. The residue remaining after the solvent has been removed in vacuo is purified by recrystallization or chromatography. In some instances, the product can be isolated directly by filtration of the reaction mixture to collect the insoluble product.

The second procedure involves contacting, in an anhydrous reaction-inert solvent such as acetone, the appropriate 3-acyl-azaoxindole-1-carboxamide (or N-substituted carboxamide), a three-fold molar excess of the requisite alpha-chloroalkylcarbonate, a five fold molar excess of sodium iodide and a two fold molar excess of anhydrous potassium carbonate, and heating the reaction mixture at about the reflux temperature of the solvent for about 16 hours. The reaction mixture is then diluted with water and the product extracted with a water-immiscible solvent such as diethyl ether or chlorform. Concentration of the solvent containing the product provides the crude material, which can be purified by recrystallization and/or chromatography.

In each of the above reactions, pressure is not critical. Pressures of about 0.5 atm to about 50 atm are generally suitable, and a pressure of 1 atm is generally preferred as a matter of convenience.

The acid addition salts of the compounds of formula I are prepared in a conventional manner by treating a solution or suspension of the free base (I) with about one chemical equivalent of a pharmaceutically acceptable acid. Conventional concentration and recrystallization techniques are employed in isolating the salts. The base addition salts of the compounds of formula I may be prepared in a conventional manner by reacting such compounds of the formula I with about one chemical equivalent of an organic or inorganic base.

The ability of the compounds of formula I to inhibit interleukin-1 biosynthesis may be determined by the assay procedure described below.

C3H/HeN mice (Charles River, Wilmington, Massachusetts) are sacrificed by cervical dislocation and their abdomens sprayed with 70% ethanol to prevent bacterial contamination of the subsequent cellular preparation. Into the peritoneum of each mouse is injected 8 ml of RPMI[1] containing 5% FCS[2], penicillin streptomycin (100 units/ml–100 ug/ml) and glutamine (2 mM). The peritoneum is kneaded to help free cells. Then, an incision through the skin of the abdomen is made to expose the underlying muscle layer. The peritioneal fluid is removed with 20 gauge needle by inserting the needle, bevel down, through the exposed muscle layer just below the sternum. The peritoneal fluid from six mice is pooled in a plastic conical tube and microscopically examined for bacterial contamination. Uncontaminated fluid is centrifuged at about 600×g for six minutes and the supernatant decanted. The pelleted cells from five to six tubes are combined and resuspended in a total of 20 ml of RPMI-FCS[3]. The cell number is then ascertained using a hemacytometer and cell viability determined with Trypan Blue staining also using a hemacytometer. The cells are then diluted to $3 \times 10^6$ cells/ml using RPMI-FCS. To the wells of a 35 mm well plate is added 1 ml of the above cell suspension. The cells are incubated for 2 hours at 37° C. In a 5% $CO_2$ atmosphere to cause adherence of the macrophages to the walls of the wells. The supernatant is removed by swirling the wells vigorous and decanting. The adherent cells (i.e., macrophages) are washed twice with RPMI-SF[4]. To the wells containing adherent cells is added 1 ml of the compound under study at concentrations ranging from 0.1 to 100 ug/ml in RPMI-SF or 1 ml of RPMI-SF as a control. Then 100 ul of LPS[5] in RPMI-SF (1 mg/5 ml) is in a 5% $CO_2$ atmosphere for 24 hours. The supernatants are removed and either assayed for IL-1 immediately or otherwise refrigerated or frozen for subsequent assay.

[1]RPMI-1640 medium (Hazelton Research Products, Inc., Lenexa, Kans.)
[2]Fetal calf serum which has been screened for good responsiveness to IL-1 in the thymyocyte assay (hyclone Laboratories, Logan, Utah) and for low spontaneous proliferation in the absence of IL-1. added to each well. The plates are incubated at 37° C.
[3]RPMI-1640 medium containing 5% fetal calf serum.
[4]RPMI containing penicillin-streptomycin (100 units/ml–100 ug/ml) and glutamine (2 mM).
[5]Refined purified lipopolysaccharide from *Salmonella minnesota* which has been checked to determine that the C3H/HeJ mouse is unresponsive thereto.

The supernatants are assayed quantitatively for IL-1 according to the receptor binding assay described below. A standard curve is generated as follows. EL4-6.1 murine thymoma cells [$10-15 \times 10^6$ cells in 0.4 ml binding buffer (RPMI 1640, 5% FCS, 25 mM HEPES, 0.01% $NaN_3$, pH 7.3)] are added to varying amounts of unlabeled murine rIL-1 [recombinant IL-1 produced in *Escherichia coli* from the published sequence of amino acids 115-270 for IL-1, Lomedico, P. M., et al., Nature, 312, 458–462 (1984)] (40 pg to 40 ng in 0.5 ml buffer) and incubated for 1 hour at 4° C. with continuous shaking, after which 0.8 ng (0.1 ml) of human $^{125}$I-rIL-1 (New England Nuclear, Boston, Mass.) is added and shaking continued for an additional 3 hours. Samples are filtered with a Yeda apparatus (Linca Co., Tel-Aviv, Israel) through Whatman GF/C2.4 cm glass fiber filters (blocked with 0.5% powdered milk for 2 hours at 37° C.) and washed once with 3 ml of ice-cold buffer. Filters are counted in a Searle gamma counter and non-specific binding is taken as the compound in the presence of 200 ng unlabeled rIL-1. A hill calibration curve is constructed by plotting log (Y/100-Y) vs. log C where Y represents the percent of control $^{125}$I-rIL-1 binding and C is the concentration of unlabeled rIL-1. A linear least-squares line is fitted through Y values between 20 to 80%. Then, to quantitate IL-1 levels in the supernatants obtained as described above, diluted supernatants replace rIL-1 in the above protocol and measured percent binding values are used to determine IL-1 concentrations from a standard Hill plot. Each dilution is assayed in duplicate and generally only dilutions with Y values being 20 to 80% are used to calculate average IL-1 levels.

The ability of the compounds of formula I to inhibit prostaglandin $H_2$ synthase and 5-lipoxygenase may be determined by the following assay procedure. By this procedure, the levels of known products of prostaglandin $H_2$ synthase and 5-lipoxygenase are measured for cells treated with the compound under study with inhibition of prostaglandin $H_2$ synthase and/or 5-lipoxygenase being evidenced by a decrease in the amount of, or absence of, the known products of those enzymes.

RBL-1 cells, maintained in monolayer, are grown for 1 to 2 days in Spinner culture in Minimum Essential Medium (Eagle) with Earle's Salts plus 15% fetal bovine serum supplemented with antibiotic/antimycotic solution (Gibco) according to the method of Jakschik, B. A., et al., Nature 287:51–52 (1980). The cells are washed twice and resuspended in cold RPMI 1640 to a cell density of $4 \times 10^6$ cells/ml. Then, a 0.25 ml aliquot of the compound under study at the desired concentration in RPMI 1640 is equilibrated at 37° C. for 5 minutes. To the eqilibrated aliquot is added a 0.25 ml aliquot of prewarmed cell suspension and the mixture is incubated at 37° C. for 5 minutes. A 10 ul solution containing $^{14}$C-arachidonic acid and A-23187 (calcium ionophore, Sigma Chemical) is added and the mixture is incubated at 37° C. for another 5 minutes. Then, 267 ul of acetonitrile/0.3% acetic acid is added and the mixture is allowed to stand on ice for 30 minutes. The tube containing the mixture is vortexed, clarified by centrifugation (3000 rpm, 10 minutes) and the supernatant is decanted and re-centrifuged for 2 minutes in a microfuge at high speed. A 100 ul aliquot of the supernatant then is analyzed by HPLC on a Perkin Elmer-HS (3 micron) column using a gradient solvent system of acetonitrile/$H_2O$ with 0.1% trifluoroacetic acid and a flow rate of 2 ml/min. Radioactivity detection is accomplished with a Berthold LB504 Radioactivity Monitor equipped with an 800 ul flow cell mixing 2.4 ml/min of Omnifluor (Trademark of New England Nuclear, Boston, Mass.) with the column effluent. Quantitation of the eluted radioactivity is carried out by the use of a Spectra Physics SP4200 computing integrator. The data so obtained is used in a data-reduction program where the integration units for each product are calculated as percent of the total integration units and compared to average control levels.

The analgesic activity of the compounds of formula I may be determined in mice by showing blockage of the abdominal stretching induced by administration of 2-phenyl-1,4-benzoquinone (PBQ), according to the method of Siegmund et al., *Proc. Soc. Exp. Biol. Med.*, 95, 729–731, (1957), adapted for high throughput as described by Milne and Twomey, *Agents and Actions*, 10, 31–37, (1980).

The antiinflammatory activity of the compounds of formula I may be demonstrated in rat by the standard carrageenin induced rat foot edema test (Winter et al., Proc. Soc. Exp. Biol. Med., 111, 544 (1963)).

When a compound of formula I or a pharmaceutically-acceptable salt thereof is to be used as an inhibitor of IL-1, an analgesic agent or an antiinflammatory agent, it can be administered to a mammalian subject either alone, or, preferably, in combination with pharmaceutically-acceptable carriers or diluents in a pharmaceutical composition, according to standard pharmaceutical practice. The compound can be administered orally or parenterally. Parenteral administration includes intravenous, intramuscular, intraperitoneal, subcutaneous and topical administration.

In a pharmaceutical composition comprising a compound of formula I, or a pharmaceutically-acceptable salt thereof, the weight ratio of carrier to active ingredient will normally be in the range from 1:4 to 4:1, and preferably 1:2 to 2:1. However, in any given case the ratio chosen will depend on such factors as the solubility of the active component, the dosage contemplated and the precise route of administration.

For oral use of a compound of formula I of this invention, the compound can be administered, for example, in the form of tablets or capsules, or as an aqueous solution or suspension. In the case of tablets for oral use, carriers which are commonly used include lactose and corn starch. Lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared and the pH of the solutions should be suitably adjusted and buffered. For intravenous use, the total concentration of solutes should be controlled to render the preparation isotonic.

When a compound of formula I or salt thereof is used in a human subject, the daily dosage will normally be determined by the prescribing physician. Moreover, the dosage will vary according to the age, weight and response of the individual patient, as well as the severity of the patient's symptoms and the potency of the particular compound being administered. However, for acute administration to relieve pain, an effective analgesic response eliciting dose in most instances will be about 5 mg to 500 mg as needed (e.g., every four to twenty-four hours). For chronic administration to alleviate inflammation and pain or inhibit IL-1 biosynthesis, an effective dose in most instances will be from about 5 mg to 1.0 g per day, and preferably 50 mg to 500 mg per day, in single or divided doses.

The following Examples illustrate the invention. All melting points referred to in the Examples are uncorrected. Except where otherwise stated, all reactions were run under a nitrogen atmosphere.

EXAMPLE 1

5-Chloro-3(2-thenoyl)-4-azaoxindole-1-N-t-butylcarboxamide

A. 5-Chloro-4-azaoxindole

In a dry flask fitted with a nitrogen inlet and mechanical stirrer was placed sodium hydride as a 60% suspension in oil (12.8 g, 0.32 mol). Most of the oil was removed by washing twice with hexanes. The remaining solid sodium hydride was then suspended in dry 1,2-dimethoxyethane (DME)(350 mL). To the resulting slurry was added dropwise with stirring a solution of diethyl malonate (49.3 mL, 0.325 mol) in DME (175 mL). The mixture was stirred at room temperature for 1 hour after which a solution of commercially available 2,6-dichloro-3-nitropyridine (25 g, 0.13 mol) in DME (175 mL) was added to give a dark red solution. Stirring at room temperature was continued overnight and the reaction mixture was poured into water. Following acidification to pH 3 with a 6N HCl solution, the mixture was extracted with ether. The ether phase was washed with brine, dried over $MgSO_4$ and concentrated in vacuo to leave a yellow oil. (Heating at 60° C. under high vacuum removed most of the excess diethyl malonate.) The $^1H$ NMR spectrum showed the residue to consist of a 2:1 mixture of 2-bis(ethoxycarbonyl)methyl-6-chloro-3-nitropyridine, the unwanted isomer 6-bis(ethoxycarbonyl)methyl-2-chloro-3-nitropyridine (arising from displacement of the chlorine atom on the 6-position of the starting material) as well as some residual diethyl malonate. The mixture was subjected to flash chromatography on silica gel using 4:1 hexane/ethyl acetate as eluant. All fractions containing the desired product were combined and concentrated to yield an oil containing 2-bis(ethoxycarbonyl)methyl-6-chloro-3-nitropyridine, 6-bis(ethoxycarbonyl)methyl-2-chloro-3-nitropyridine and diethyl malonate in a molar ration of approximately 10:4:3 weighing 40.5 g. The yield of 2-bis(ethoxycarbonyl)methyl-6-chloro-3-nitropyridine was thus calculated to be approximately 26 g, (63%).

The mixture of 2-bis(ethoxycarbonyl)methyl-6-chloro-3-nitropyridine, 6-bis(ethoxycarbonyl)methyl-2-chloro-3-nitropyridine and diethyl malonate was dissolved in ethanol (300 mL) and added to a suspension of 50% Raney nickel in water (26 g) diluted with ethanol (700 mL). The mixture was hydrogenated in Parr shaker at 3 atmospheres pressure for 4 hours and then filtered through diatomaceous earth to remove the catalyst. The solvent was removed in vacuo to leave a mixture of 3-amino-2-bis(ethoxycarbonyl)methyl-6-chloropyridine, 3-amino-6-bis(ethoxycarbonyl)-methyl-2-chloropyridine—the unwanted isomer, and diethyl malonate as a waxy solid (35.7 g).

The mixture containing 3-amino-2-bis(ethoxycarbonyl)methyl-6-chloropyridine, 3-amino-6-bis(ethoxycarbonyl)methyl-2-chloropyridine and diethyl malonate was taken up in 6N HCl solution (700 mL) and heated at reflux for 5 hours. After removing the aqueous acid in vacuo, the residue was taken up in water and again concentrated to yield 5-chloro-4-azaoxindole as a brown solid which was dried in the air. The yield was 7.04 g. (32% overall from 2,6-dichloro-3-nitropyridine). An analytical sample was prepared by recrystallization from isopropanol; m.p. 250°–254° C. (dec.).

B. 5-Chloro-3-(2-thenoyl)-4-azaoxindole

Pellets of sodium metal (2.0 g, 87.0 mmol) were added to dry ethanol (50 mL) in a dry round-bottomed flask. When dissolution of the sodium was complete, solid 5-chloro-4-azaoxindole (3.0 g, 17.8 mmol) was added followed by ethyl 2-thiophenecarboxylate (4.8 mL, 40 mmol). The mixture was heated at reflux overnight under nitrogen. During this period, a precipitate formed. The mixture was cooled, poured into ice/water and acidified to pH 3 with 6N HCl solution. The solid product (3.7 g, 75%, m.p. 235°–238° C.) was collected by filtration washing with water and ether. A second crop of product (375 mg, 8%, m.p. 240°–241° C.) crystallized from the filtrate and was collected.

C. 5-Chloro-3-(2-thenoyl)-4-azaoxindole-1-N-t-butyl carboxamide

To a solution of 5-chloro-3-(2-thenoyl)-4-azaoxindole (500 mg, 1.79 mmol) in dry DMSO (10 mL) was added sequentially triethylamine (0.54 mL, 3.87 mmol) and t-butylisocyanate (0.3 mL, 2.63 mmol). The resulting mixture was heated under nitrogen in an oil bath at 85° C. for 3 hours. After cooling to room temperature, the solution was poured into ice/water and acidified to pH 2 by addition of 6N HCl solution. The insoluble solid was collected by filtration. This was subjected to flash chromatography on two successive silica gel columns using ethyl acetate as eluant for the first column and 20% hexane/chloroform as eluant for the second. Recrystallization of the chromatographed material from acetonitrile afforded the title compound (300 mg, 44%) as a yellow solid; m.p. 150°–152° C. $^1H$ NMR (DMSO-$d_6$): δ9.00 (s, 1H), 8.83 (d, J=3.6 Hz, 1H), 8.35 (d, J=8.1 Hz, 1H), 8.00 (d, J=4.9 Hz, 1H), 7.28–7.25 (m, 1H), 7.24 (d, J=8.1 Hz, 1H), 1.40 (s, 9H). IR (KBr disc) 1713, 1647, 1582, 1461 cm$^{-1}$. MS m/e (relative percent) 379 (4), 377 (18), 280 (23), 278 (70), 196 (38), 194 (100), 111 (12). Analysis calc'd for $C_{17}H_{16}ClN_3O_3S$: C 54.04, H, 4.27, N 11.12. Found: C 53.59, H 4.01, N 10.92.

EXAMPLE 2

6-Chloro-3-(2-thenoyl)-4-azaoxindole-1-carboxamide

A. 6-Chloro-4-azaoxindole 2,5-Dichloro-3-nitropyridine was prepared from 2-hydroxy-3-nitro-5-chloropyridine following the procedure of *Chem. Abs.,* 70, 68286y (1969). 2-Hydroxy-3-nitro-5-chloropyridine was prepared by nitration of commercially available 2-hydroxy-5-nitropyridine ($H_2SO_4/HNO_3/60°$). This route proved to be cleaner and higher yielding than the published procedure (*Chem. Abs.,* 70, 68286y (1969)) involving nitration of 2-amino-5-chloropyridine.

In a dry flask fitted with a nitrogen inlet and mechanical stirrer was placed sodium hydride as a 60° suspension in oil (4.0 g, 0.10 mol). Most of the oil was removed by washing twice with hexanes. The remaining solid sodium hydride was then suspended in dry 1,2-dimethoxyethane (DME) (125 mL). To the resulting slurry was added dropwise, with stirring, a solution of diethyl malonate (15.7 mL, 0.10 mol) in DME (50 mL). The mixture was stirred at room temperature for 1 hour after which a solution of 2,5-dichloro-3-nitropyridine (10 g, 51.8 mmol) in DME (75 mL) was added. Stirring at room temperature was continued overnight and the reaction mixture was diluted with water. Following acidification to pH 2 with 1N HCl solution, the mixture was extracted with ether. The ether phase was washed with brine, dried over $MgSO_4$ and concentrated in vacuo to leave a red oil. This was subjected to flash chromatography on silica gel using 9:1 hexane/ethyl acetate as eluant. All fractions containing the desired product were combined and concentrated to yield 2-bis(ethoxycarbonyl)methyl-5-chloro-3-nitropyridine as an oil (13.6 g, 82%).

A solution of the diester in ethanol (200 mL) was added to a suspension of 50% Raney nickel in water (8.8 g) diluted with ethanol (300 mL). The mixture was hydrogenated in a Parr shaker at 3 atmospheres pressure for 4 hours and then filtered through diatomaceous earth to remove the catalyst. The solvent was removed in vacuo to leave 3-amino-2-bis (ethoxycarbonyl)methyl-5-chloropyridine as light yellow solid (12.6 g).

A mixture of 3-amino-2-bis(ethoxycarbonyl)methyl-5-chloropyridine and 6N HCl (325 mL) was heated at reflux for 4 hours. After removing the aqueous acid in vacuo, the residue was taken up in water and filtered to remove a small amount of black insoluble material. On adjustment of the filtrate to pH 6.5 with solid $NaHCO_3$, 6-chloro-4-azaoxindole precipitated as a tan solid (2.6 g) which was collected by filtration. The filtrate was extracted with ethyl acetate and the combined extracts were dried ($MgSO_4$) and concentrated to yield an additional quantity of 6-chloro-4-azaoxindole (3.6 g). The total yield was thus 6.2 g (71% overall from 2,5-dichloro-3-nitropyridine).

B. 6-Chloro-3-(2-thenoyl)-4-azaoxindole

Pellets of sodium metal (3.4 g, 0.15 mmol) were added to dry ethanol (90 mL) in a dry round-bottomed flask. When dissolution of the sodium was complete, solid 6-chloro-4-azaoxindole (5.0 g 29.7 mmol) was added followed by ethyl 2-thiophenecarboxylate (8 mL, 55 mmol). The mixture was heated under nitrogen at reflux overnight during which a precipitate formed. The mixture was cooled, poured into ice/water and acidified to pH 3 with 6N HCl solution. The solid azaoxindole (7.8 g, 94%) (m.p. 250°) was collected by filtration washing with water and ether and dried in vacuo with heating.

C. 6-Chloro-3-(2-thenoyl)-4-azaoxindole-1-carboxamide

A mixture of 6-chloro-3-(2-thenoyl)-4-azaoxindole (3.3 g, 11.8 mmol) and dry acetonitrile (100 mL) was cooled to 0° and treated with N-chlorosulfonylisocyanate (1.5 mL, 17.2 mmol). The mixture was stirred at room temperature for 6 hours and then poured into ice/water. The solid was collected by filtration, washed with water, and then stirred in water at 100° for 20 minutes. The product was collected by filtration and dried. Recrystallization from acetic acid provided analytically pure 6-chloro-3-(2-thenoyl)-4-azaoxindole-1-carboxamide, m.p.>250° C. $^1$H NMR (DMSO-$d_6$): δ8.78 (d, J=3 Hz, 1H), 8.57 (br s, 1H), 8.39 (s, 1H), 7.92–7.89 (m, 3H), 7.23–7.21 (m, 1H). IR (KBr disc) 1721, 1602, 1420 cm$^{-1}$. MS m/e (relative percent) 321 (13), 280 (11), 278 (36), 196 (40), 194 (100), 111 (333). Analysis calc'd for $C_{13}H_8ClN_3O_3S$: C 48. 53, H 2.51, N 13.06. Found: C 48.58, H 2.42, N 12.95.

EXAMPLE 3

5-Chloro-3-(2-thenoyl)-6-azaoxindole-1-N-t-butylcarboxamide

A. (5-Amino-2-chloro-4-pyridyl) acetonitrile

To a stirred solution of potassium t-butoxide (24.69 g, 220 mmol, 2.2 eq) in anhydrous tetrahydrofuran (150 ml) at −50° C. under nitrogen, a solution of 2-chloro-5-nitropyridine (15.85 g, 100 mmol) and (4-chlorophenoxy)acetonitrile (E. Grochowski et al., *Bull. Acad. Pol. Sci. Ser. Sci. Chim.,* 11, 443 (1963)) (18.44 g, 110 mmol, 1.1 eq) in anhydrous tetrahydrofuran (150 ml) was added dropwise at such a rate that the reaction temperature was maintained at −40° to −50° C. with cooling in a dry ice/acetone bath. The resultant purple colored reaction mixture was then stirred at −78° C. under nitrogen for 1 hour, at which time glacial acetic acid (20 ml, 0.35 mol, 3.5 eq) was added to the reaction, and the mixture was allowed to warm to room temperature. A solution of 5% HCl (100 ml) was added to the reaction mixture and this aqueous mixture was extracted with ethyl ether (100 ml) and then with methylene chloride (2×100 ml). The extracts were combined, dried over magnesium sulfate, and passed through a silica gel filter (approximately 150 g) followed by methylene chloride (1200 ml). This filtrate was evaporated under reduced pressure, and the residual oil was chromatographed using silica gel (approximately 300 g) and eluted with 25% hexanes in methylene chloride to afford an oil ($R_f$=0.52 in methylene chloride) which was triturated in cold anhydrous ether to afford 6-chloro-3-nitro-2-pyridyl acetonitrile (1.37 g, 7%) as a white crystalline solid: mp, 121.5°–123.5° C. Further elution yielded another oil ($R_f$= 0.48 in methylene chloride) which was triturated with cold anhydrous ethyl ether to afford (2-chloro-5-nitro-4-pyridyl) acetonitrile (1.87 g, 9%) as a white crystalline solid, m.p. 87°–89° C. IR (KBr) 3080, 2240, 1600, 1545, 1520, 1450, 1390, 1340, 1135 cm$^{-1}$.

A solution of (2-chloro-5-nitro-4-pyridyl) acetonitrile in ethanol (100 mL) was added to a suspension of 50% Raney nickel in water (3.2 g) diluted with ethanol (150 mL). The mixture was hydrogenated in a Parr shaker at 3 atmospheres pressure for 2.5 hours and then filtered through Celite® (diatomaceous earth) to remove the catalyst. The solvent was removed in vacuo to leave a dark oil which was subjected to flash chromatography on silica gel using 3:1 ethyl acetate/hexanes as eluant. Fractions containing only the title compound were combined and concentrated to afford an oil (850 mg, 32%). Less pure fractions were also combined and concentrated to give an oil (600 mg) of which the title compound was the major component (about 75%).

B. 5-Chloro-6-azaoxindole (5-Amino-2-chloro-4-pyridyl)acetonitrile (1.40 g, 8.4 mmol) was taken up in 6N HCl solution (100 mL) and heated between 50° and 100° C. for 2 hours. After cooling, the solution was adjusted to pH 7 by addition of solid NaHCO$_3$ and extracted with ethyl acetate. The combined ethyl acetate extracts were washed with brine, dried over MgSO$_4$ and concentrated in vacuo. The residue was subjected to flash chromatography on silica gel using ethyl acetate as eluant. (Some methanol was used to help dissolve the solid). Fractions containing the desired product were combined and concentrated to leave the title compound as a solid (650 mg, 46%), m.p. 230° C. (dec.) The NMR spectrum indicated that this material contained a small amount of the by-product, 2-amino-5-chloro-6-azaindole in addition to the title compound. Nonetheless, this material was used in the next step without further purification.

C. 5-Chloro-3-(2-thenoyl)-6-azaoxindole

Pellets of sodium metal (232 mg, 10 mmol) were added to dry ethanol (10 mL) in a dry round-bottomed flask. When dissolution of the sodium was complete, solid 5-chloro-6-azaoxindole (340 mg, 2.0 mmol) was added followed by ethyl 2-thiophenecarboxylate (0.54 mL, 4.0 mmol). The mixture was heated under nitrogen at reflux overnight during which a precipitate formed. The mixture was cooled, poured into ice/water and acidified to pH 4 with 6N HCl solution. The solid product (475 mg) was collected by filtration, washed with water, and dried in the air. This material was recrystallized from methanol to afford the title compound (190 mg, 34%). $^1$H NMR (DMSO-d$_6$): δ10.62 (br s, 1H), 8.79 (d, J=3.2 Hz, 1H), 7.92 (s, 1H), 7.77 (d, J=5 Hz, 1H), 7.65 (s, 1H), 7.17–7.14 (m, 1H).

D. 5-Chloro-3-(2-thenoyl)-6-azaoxindole-1-N-t-butylcarboxamide

To a solution of 5-chloro-3-(2-thenoyl)-6-azaoxindole (190 mg, 0.68 mmol) in dry DMSO (3 mL) was added sequentially triethylamine (0.20 mL 1.44 mmol) and t-butylisocyanate (0.11 mL, 0.96 mmol). The resulting mixture was heated under nitrogen in an oil bath at 85° C. for 4 hours. The solution was cooled to room temperature and then poured into ice/water and acidified to pH 2 by addition of 1N HCl solution. The insoluble solid was collected by filtration, dried in the air and recrystallized from methanol to afford the desired product (175 mg, 68%), m.p. 224° C. (dec.). $^1$H NMR (DMSO-d$_6$): δ9.45 (s, 1H), 8.70 (s, 1H), 8.43 (dd, J=1.2, 3.4 Hz, 1H), 8.06 (s, 1H), 7.82 (dd, J=1.2, 4.9 Hz, 1H), 7.18 (dd, J=3.4, 4.9 Hz, 1H), 1.40 (s, 9H). IR (KBr disc) 1723, 1660, 1624, 1586, 1552, 1474 cm$^{-1}$. Ms m/e (relative percent) 377 (2), 280 (21), 278 (59), 196 (41), 194 (100), 111 (41). Analysis calc'd for C$_{17}$H$_{16}$ClN$_3$O$_3$S: C 54.04, H 4.27, N 11.12. Found: C 53.88, H 4.21, N 11.04.

EXAMPLE 4

3-(2-Thenoyl)-5-azaoxindole-1-N-t-butylcarboxamide

A. 3,3,7-Tribromo-5-azaoxindole

The starting material for the synthesis of 3,3,7-tribromo-5-azaoxindole was 5-azaindole, prepared as described in U.S. Pat. No. 4,625,033. Alternatively, this material may be prepared as described by Yamanaka et al. (Chem. Pharm. Bull., 35, 1823 (1987)) or by Okuda and Robison (J. Org. Chem., 24, 1008 (1959)). To a stirred solution of 5-azaindole (1.5 g, 12.7 mmol) in t-butanol (100 ml) and H$_2$O (100 ml) at room temperature was added dropwise neat Br$_2$ (2.6 ml, 50.5 mmol) over a period of 20 minutes. Following addition of Br$_2$, the pH of the mixture was approximately 1. By the careful, slow addition of a saturated aqueous NaHCO$_3$ solution over 0.5 hour, the pH of the mixture was then adjusted to 6.5–7. During this period, precipitation became evident. The precipitate was collected by filtration of the reaction mixture, washed with water, and dried in the air to yield 3.7 g (79%) of a yellow solid, m.p. 250° C. By extraction of the filtrate with ethyl acetate, more of the title compound (700 mg, 15%) was obtained; however this sample was somewhat less pure as determined by TLC. Combined impure fractions from several runs were purified by flash chromatography on silica gel using 10% methanol/CHCl$_3$ as eluant.

B. 5-Azaoxindole

To a solution of 3,3,7-tribromo-5-azaoxindole (6.4 g, 17.3 mmol) in ethanol (1200 ml) was added 10% Pd on charcoal (3.2 g). The mixture was hydrogenated under 3 atm. hydrogen gas for 3 hours using a Parr shaker. The catalyst was removed by filtration of the mixture through a pad of Celite®, washing well with ethanol. On removal of the solvent, a brown solid remained (predominantly the hydrobromide of the desired product), 3.5 g. This was dissolved in water, treated with activated charcoal and filtered through Celite®. The pH of the filtrate was adjusted to 7.5 by the addition of saturated aqueous NaHCO$_3$ solution. The mixture was then extracted with n-butanol (3×). The combined n-butanol extracts were washed with brine, dried over magnesium sulfate and concentrated in vacuo to leave a solid. This was triturated with butanone and filtered to collect 5-azaoxindole as a tan solid (1.6 g, 69%). After removal of butanone, the mother liquor yielded a solid which was recrystallized from methanol to yield more of the title compound (50 mg), m.p.>250° C.

C. 3-(2-Thenoyl)-5-azaoxindole

Pellets of sodium metal (1.15 g, 50 mmol) were added to dry ethanol (30 mL) in a dry round-bottomed flask. When dissolution of the sodium was complete, solid 5-azaoxindole (1.40 mg, 10.4 mmol) was added followed by ethyl 2-thiophenecarboxylate (2.7 mL, 20.1 mmol). The mixture was heated under nitrogen at reflux for 1 hour. At this point, the volume of the mixture was reduced 50% by distillation of ethanol at atmospheric pressure. The mixture was cooled and poured into ice/water. The resulting solution was filtered to remove a small amount of insoluble material which was washed well with water. Upon acidification of the filtrate to pH 7 with 6N HCl solution, the product precipitated. This was collected by filtration, washed with water and dried in the air to yield the title compound as a yellow/brown solid (2.0 g, 83%).

D. (2-Thenoyl)-5-azaoxindole-1-N-t-butylcarboxamide

To a solution of 3-(2-thenoyl)-5-azaoxindole (500 mg, 2.05 mmol) in dry DMSO (10 mL) was added sequentially triethylamine (0.60 mL, 4.3 mmol) and t-butylisocyanate (0.35 mL, 3.06 mmol). The resulting mixture was heated under nitrogen in an oil bath at 85° C. for 5 hours. After cooling to room temperature, the solution was poured into ice/water and acidified to pH 2 by addition of 6N HCl solution. The insoluble solid was collected by filtration, washed with water and dried in the air. The crude product was subjected to flash chromatography on silica gel using chloroform/methanol (9:1). Fractions containing the desired product were combined and concentrated to leave a solid. This was recrystallized from methanol/chloroform/acetonitrile and then from chlorform/methanol to afford the title compound (210 mg, 31%), m.p.>250° C. $^1$H NMR (DMSO-d$_6$): δ9.85 (s, 1H), 9.18 (s, 1H), 8.70 (dd, J=1.6, 3.5

Hz, 1H), 8.41 (d, J=6.2 Hz, 1H) 8.26 (d, J=6.2 Hz, 1H), 7.73 (dd, J=1.6, 4.9 Hz, 1H), 7.16 (dd, J=3.5, 4.9 Hz, 1H), 1.41 (s, 9H). IR (KBr disc) 1723, 1653, 1615, 1549, 1474, 1427 cm$^{-1}$. MS m/e (relative percent) 343 (2), 244 (30), 160 (90), 111 (28), 84 (100). Analysis calc'd for $C_{17}H_{17}N_3O_3S$: C 59.46, H 4.99, N 12.24. Found: C 58.68, H 4.87, N 11.54.

EXAMPLE 5

5-Fluoro-3-(2-thenoyl)-4-azaoxindole-1-N-t-butylcarboxamide

A. 5-Fluoro-2-hydroxy-3-nitropyridine

5-Fluoro-2-hydroxypyridine (5-fluoro-2-pyridone) was prepared from commerially available 5-amino-2-fluoropyridine as described by Nesnow and Heidelberger (*J. Heterocyclic Chem.,* 10, 779 (1973)) except that refluxing 48% hydrobromic acid was used to carry out the final hydrolysis of 2-fluoro-5-methoxypyridine rather than the literature conditions (25% hydrochloric acid in a sealed glass tube at 145° C.). 5-Fluoro-2-hydroxypyridine (11.16 g, 98.7 mmol) was added in portions to concentrated sulfuric acid (90 mL) at 0° C. Fuming nitric acid was then added dropwise. The reaction mixture was allowed to warm to room temperature and was then heated at 55°–60° C. for 3 hours. The mixture was cooled to room temperature and was then poured into ice/water. The yellow product was collected by filtration, washed with water and dried in the air to yield 8.24 g (53%) of the title compound. The filtrate was adjusted to pH 2 by the addition of solid $NaHCO_3$ and was extracted with ethyl acetate. The combined extracts were dried ($MgSO_4$) and concentrated to yield an additional amount of the title compound (1.71 g, 11%).

B. 2-Chloro-5-fluoro-3-nitropyridine

To a mixture of phosphorus pentachloride (9.41 g, 45.2 mmol) and phosphorus oxychloride (4.2 mL, 45.1 mmol) at 60° C. was added in portions 5-fluro-2-hydroxy-3-nitropyridine (6.5 g, 41.1 mmol). The mixture was stirred in an oil bath at 100° C. under nitrogen overnight, cooled to room temperature and poured into ice/water. After addition of more water and ethyl acetate, the mixture was filtered through Celite® to remove dark insoluble material. The organic phase was washed with brine, filtered again to remove more dark material, dried over $MgSO_4$ and concentrated. The residue was subjected to flash chromatography on silica gel using chlorform as eluant. Fractions containing the title compound were combined and concentrated to provide a yellow oil (3.51 g, 48%) which solidified on standing at 5° C. overnight.

C. 6-Fluoro-4-azaoxindole

In a dry flask was placed sodium hydride as a 60% suspension in oil (3.1 g, 77.5 mmol). Most of the oil was removed by washing twice with hexanes. The remaining solid sodium hydride was then suspended in dry dimethylformamide (DMF) (100 mL) and cooled to 0° C. Diethyl malonate (11.8 mL, 77.7 mmol) was then added dropwise with stirring. The mixture was stirred at 0° C. for 1 hour after which a solution of 2-chloro-5-fluoro-3-nitropyridine (5.21 g, 29.5 mmol) in DMF (40 mL) was added. Stirring at room temperature was continued overnight and the reaction mixture was poured into ice/water. Following acidification to pH 3 with 6N HCl solution, the mixture was extracted with ethyl acetate. The organic phase was washed with brine, dried over $MgSO_4$ and concentrated in vacuo to leave a red oil. This was subjected to flash chromatography on silica gel using 3:7 ethyl acetate/hexanes, as eluant. All fractions containing the desired product were combined and concentrated to yield an oil containing 2-bis(ethoxycarbonyl)methyl-5-fluoro-3-nitropyridine and diethyl malonate in a molar ratio of approximately 11:9 weighing 11.5 g. The yield of 2-bis(ethoxycarbonyl)methyl-5-fluoro-3-nitropyridine was calculated to be approximately 8 g (90%).

The mixture of 2-bis(ethoxycarbonyl)methyl-5-fluoro-3-nitropyridine and diethyl malonate was dissolved in ethanol (100 mL) and added to a suspension of 50% Raney nickel in water (7.8 g) diluted with ethanol (150 mL). The mixture was hydrogenated in a Parr shaker at 3 atmospheres pressure overnight and then filtered through diatomaceous earth (Celite (trademark)) to remove the catalyst. The solvent was removed in vacuo to leave a mixture of 3-amino-2-bis(ethoxycarbonyl)methyl-5-fluoropyridine and diethyl malonate as an oil. The mixture containing 3-amino-2-bis(ethoxycarbonyl)methyl-5-fluropyridine and diethyl malonate was taken up in 6N HCl solution (280 mL) and heated at reflux for 3 hours. After removing the aqueous acid in vacuo, the residue was taken up in water and again concentrated to leave a solid. This was taken up in dry ethanol and concentrated two times to obtain the title compound as a light green solid (4.07 g) which was triturated with hot ethyl acetate and dried in the air. Although somewhat impure by NMR this material was used in directly in the next step without further purification.

D. 5-Fluoro-3-(2-thenoyl)-4-azaoxindole

Pellets of sodium metal (0.75 g, 32.6 mmol) were added to dry ethanol (30 mL) in a dry round-bottomed flask. When dissolution of the sodium was complete, solid 6-fluoro-4-azaoxindole (1.0 g, 6.57 mmol) was added followed by ethyl 2-thiophenecarboxylate (4.8 mL, 13.4 mmol). The mixture was heated at reflux for 2 days under nitrogen. During this period, a yellow precipitate formed. The mixture was cooled, poured into ice/water and acidified to pH 2 with 6N HCl solution. The title compound (854 mg, 50%) was collected by filtration washing with water and ether. A small second crop of product (32 mg, 2%) crystallized from the filtrate and collected.

E. 5-Fluoro-3-(2-thenoyl)-4-azaoxindole-1-N-t-butylcarboxamide

To a solution of 5-fluoro-3-(2-thenoyl)-4-azaoxindole (450 mg, 1.72 mmol) in dry DMSO (15 mL) was added sequentially triethylamine (0.50 mL, 3.59 mmol) and t-butylisocyanate (0.30 mL, 2.62 mmol). The resulting mixture was heated under nitrogen in an oil bath at 85° overnight. The solution was allowed to cool to room temperature and was then poured into ice/water and acidifed to pH 2 by addition of 1N HCl solution. The insoluble green solid was collected by filtration, dried in the air and subjected to flash chromatography on silica gel using ethyl acetate as eluant. (Some acetonitrile was required to dissolve the solid). Fractions containing the desired product were combined and concentrated. The resulting solid was recrystallized from ethyl acetate/acetonitrile to afford the title compound as green needles (181 mg, 29%), m.p. 258° C. $^1$H NMR (DMSO-$d_6$): δ14.00 (br s, 1H), 9.28 (s, 1H), 8.77 (d, J=4 Hz, 1H), 8.44 (dd, J=1.9, 9.5 Hz, 1H), 7.98–7.96 (m, 1H), 7.89 (d, J=4.9 Hz, 1H), 7.24 (dd, J=4, 4.49 Hz, 1H), 1.40 (s, 9H). IR (KBr disc) 1721, 1609, 1552, 1423 cm$^{-1}$. MS m/e (relative percent) 361 (4), 262 (40), 178 (100), 111 (13). Analysis calc'd for $C_{17}H_{16}FN_3O_3S$: C 56.50, H 4.46, N 11.63. Found: C 55.86, H 4.48, N 11.41.

EXAMPLE 6

5,6-Dichloro-3-(2-thenoyl)-4-azaoxindole-1-N-t-butylcarboxamide

A. 5,6-Dichloro-4-azaoxindole

3-Nitro-2,5,6-trichloropyridine was prepared as described in *Helv. Chim. Acta,* 59, 190 (1976), starting from commercially available pentachloropyridine. The first step afforded a mixture of the desired 2,5,6-trichloropyridine and minor amounts of three tetrachloropyridine isomers. This mixture was nitrated as described in the above reference to give a mixture of 3-nitro-2,5,6-trichloropyridine, minor amounts of 2,5,6-trichloropyridine and the tetrachloropyridine isomers (which were found to be difficult to remove). In a dry flask was placed sodium hydride (7.92 g, 198 mmol) as a 60% suspension in oil, which was suspended in dry dimethylformamide (DMF) (90 mL). Diethylmalonate (24.7 mL, 180 mmol) was then added dropwise with stirring. The mixture was stirred at room temperature for 0.25 hours and cooled to 0° C. A solution of a mixture of 3-nitro-2,5,6-trichloropyridine (12.5 g, 55 mmol), 2,5,6-trichloropyridine (1.6 g) and three tetrachloropyridine isomers (total 6.4 g) in DMF (40 mL) was cooled to 0° C. and added dropwise. The mixture was stirred at 0° C. for 0.25 hours, taken up in water and acidified using 6N HCl solution.

After extracting with ether, the combined ether layers were washed with brine, dried over $MgSO_4$ and concentrated to leave an oil. This was passed through a thick pad of silica gel, washing first with hexane (to remove oil and the trichloro and tetrachloropyridines) and then with ethyl acetate to elute the mixture of products. Following removal of the solvent, the mixture was subjected to flash chromatography on silica gel using 19:1 hexane/ethyl acetate as eluant. All fractions containing the desired product were combined and concentrated to leave an oil consisting of the desired [2-bis(ethoxycarbonyl)methyl-5,6-dichloro-3-nitropyridine] (5.2 g, 27% yield), 2-bis(ethoxycarbonyl) methyl-3,6-dichloro-5-nitropyridine (10.5 g, 54% yield) and diethylmalonate.

The mixture of 2-bis(ethoxycarbonyl)methyl-5,6-dichloro-3-nitropyridine, 2-bis(ethoxycarbonyl)methyl-3,6-dichloro-5-nitropyridine and diethylmalonate was dissolved in ethanol (100 mL) and added to a suspension of 50% Raney nickel in water (30 g) diluted with ethanol (10 mL). The mixture was hydrogenated in a Parr shaker at 3 atmospheres pressure for 5 hours and then filtered through diatomaceous earth (Celite (trademark)) to remove the catalyst. The solvent was removed in vacuo to leave an oil which was subjected to flash chromatography on silica gel eluting with 4:1 hexane/ethyl acetate. Each of the fractions was separately concentrated and the residues examined by $^1$H NMR in deuterochloroform. Eluted after diethylmalonate was the desired product, 3-amino-2-bis(ethoxycarbonyl) methyl-5,6-dichloropyridine, followed closely thereafter by the unwanted isomer, 5-amino-2-bis(ethoxycarbonyl) methyl-3,6-dichloropyridine. Although clean separation from diethyl malonate was achieved, the bulk of the mass of desired product and the isomer eluted as mixed fractions. Leading fractions containing only 3-amino-2-bis (ethoxycarbonyl)methyl-5,6-dichloropyridine and mixed fractions containing at least 10% of this material were combined to afford a solid consisting of 3-amino-2-bis (ethoxycarbonyl)methyl-5,6-dichloropyridine (3.17 g) and the unwanted isomer, 3-amino-2-bis(ethoxycarbonyl) methyl-3,6-dichloropyridine (4.03 g). This mixture was taken up in 6N HCl solution (120 mL) and heated at reflux for 3 hours. After cooling to room temperature the volatiles were removed in vacuo. Ethanol was added and then evaporated to help remove water. This process was repeated. The resulting brown solid was subjected to flash chromatography on silica gel using 9:1 chloroform/methanol as eluant. All fractions containing the desired product were combined and concentrated to leave a solid which was triturated with methanol to afford 5,6-dichloro-4-azaoxindole (1.42 g, 71%) from 3-amino-2-bis(ethoxycarbonyl)methyl-5,6-dichloropyridine, 13% overall from 3-nitro-2,5,6-trichloropyridne). M.p. 230°–233° C. (dec).

B. 5,6-Dichloro-3-(2-thenoyl)-4-azaoxindole

Pellets of sodium metal (0.29 g, 12.6 mmol) were added to dry ethanol (10 mL) in a dry round-bottomed flask. When dissolution of the sodium was complete, solid 5,6-dichloro-4-azaoxindole (500 mg, 2.46 mmol) was added followed by ethyl 2-thiophenecarboxylate (0.67 mL. 5.0 mmol). The mixture was heated at reflux for one day under nitrogen. The mixture was cooled, poured into ice/water and acidified to pH 3 with 6N HCl solution. The title compound was collected by filtration and dried in vacuo to afford 607 mg (79%).

C. 5,6-Dichloro-3-(2-thenoyl)-4-azaoxindole-1-N-t-butylcarboxamide

To a solution of 5,6-dichloro-3-(2-thenoyl)-4-azaoxindole (300 mg, 0.96 mmol) in dry DMSO (8 mL) was added sequentially triethylamine (0.20 mL, 1.43 mmol) and t-butylisocyanate (0.16 mL, 1.40 mmol). The resulting mixture was heated under nitrogen in an oil bath at 85° C. for 5 hours. The solution was poured into ice/water and acidified to pH 2 by addition of 1N HCl solution. The insoluble solid was collected by filtration, dried and subjected to flash chromatography on silica gel using 99:1 chloroform/ methanol as eluant. Fractions containing the desired product were combined and concentrated. The resulting solid was recrystallized from chloroform/methanol to afford 207 mg (52%) of the title compound, m.p. 189°–190° C. $^1$H NMR (DMSO-$d_6$): δ9.66 (d, J=4 Hz, 0.4H), 9.02 (d, J=4 Hz, 0.6H), 8.84 (br s, 0.6H), 8.70 (s, 0.4H), 8.58 (s, 0.6H), 8.44 (br s, 0.4H), 7.83 (d, J=5 Hz, 0.4H), 7.76 (d, J=5 Hz, 0.6H), 7.30 (dd, J=4.5 Hz, 0.4H), 7.23 (dd, J=4.5 Hz, 0.6H), 1.47 (s, 9H). IR (KBr disc) 1712, 1640, 1579, 1534 cm$^{-1}$. Ms m/e (relative percent) 413 (1), 411 (2), 314 (30), 312 (38), 230 (75), 228 (100), 111 (38). Analysis calc'd for $C_{17}H_{15}Cl_2N_3O_3S$: C 49.52, H 3.67, N 10.19; found C 49.45, H 3.58; N 9.91.

EXAMPLE 7

3-(2-Thenoyl)-6-trifluoromethyl-4-azaoxindole-1-N-t-butylcarboxamide

A. 2-Chloro-3-nitro-5-trifluoromethylpyridine

The starting material, 2-hydroxy-3-nitro-5-trifluoromethylpyridine, was prepared as described in British Patent 1,421,619 starting from commercially available 2-chloro-5-trifluoromethylpyridine.

2-Hydroxy-3-nitro-5-trifluoromethylpyridine (8.8 g, 42.3 mmol) was added to a mixture of phosphorous oxychloride (4.2 mL, 45.9 mmol) and phosphorous pentachloride (9.6 g, 46.1 mmol) at 60° C. The reaction mixture was then heated under nitrogen at 80° C. overnight. The resulting dark product mixture was allowed to cool to room temperature and was poured into ice/water. The mixture was extracted with ether and the ether extract was washed with water and brine. After drying over magnesium sulfate, the solvent was removed to leave a dark oil which was subjected to flash chromatography on silica gel eluting with chloroform. Fractions containing only the desired product were combined and concentrated to leave a brown oil (5.0 g, 52%). $^1$H NMR (DMSO-$d_6$): δ9.20 (s, 1H), 9.07 (s, 1H).

B. 2-Bis(benzyloxycarbonyl)methyl-3-nitro-5-trifluoromethylpyridine

In a dry flask was placed sodium hydride as a 60% suspension in oil (800 mg, 2.0 mmol). Most of the oil was removed by washing twice with hexanes. The remaining solid sodium hydride was then suspended in dry 1,2- dimethoxyethane (DME) (20 mL). A solution of dibenzyl malonate (5.0 mL, 2.0 mmol) in DME (15 mL) was then added dropwise with stirring. The mixture was stirred at room temperature for 0.5 hr after which a solution of 2-chloro-3-nitro-5-trifluoromethyl pyridine (2.3 g, 10.2 mmol) in DME (15 mL) was added. Stirring at room temperature was continued overnight and the reaction mixture was poured into ice/water. Following acidification to pH 3 with 1N HCl solution, the mixture was extracted with ethyl acetate. The organic phase was washed with brine, dried over $MgSO_4$ and concentrated in vacuo to leave an oil. This was subjected to flash chromatography on silica gel using toluene as eluant. All fractions containing the desired product were combined and concentrated to leave a tan solid; 3.8 g (79%): mp 82°–84° C.

C. 3-Benzyloxycarbonyl-6-trifluoromethyl-4-azaoxindole

A mechanically stirred mixture of 2-bis(benzyloxycarbonyl)methyl-3-nitro-5-trifluoromethylpyridine (1.2 g, 2.5 mmol), iron dust (495 mg, 8.9 mmol), and glacial acetic acid (50 mL) was heated at reflux for 2 hr. After cooling, the mixture was poured into ice/water. The precipitated white solid was collected by filtration, air-dried and then dried in vacuo overnight. Yield: 780 mg (93%); mp>250° C.

D. 3-Benzyloxycarbonyl-6-trifluoromethyl-4-azaoxindole-1-N-t-butylcarboxamide

To a solution of 3-benzyloxycarbonyl-6-trifluoromethyl-4-azaoxindole (750 mg, 2.23 mmol), in dry DMSO (15 mL) was added sequentially triethylamine (0.60 mL, 4.3 mmol) and t-butylisocyanate (0.38 mL, 3.33 mmol). The resulting mixture was heated under nitrogen in an oil bath at 90°–100° C. for 5 hr. After cooling to room temperature, the solution was poured into ice/water and acidified to pH 3 by addition of a 1N HCl solution. The insoluble solid was collected by filtration and dissolved in chloroform. The resulting solution was dried over $MgSO_4$ and concentrated in vacuo. The residue was subjected to flash chromatography on silica gel eluting with chlorform. Fractions containing the desired product were combined and concentrated to leave a white solid. Yield: 830 mg (86%); mp>250° C.

E. 6-Trifluromethyl-4-azaoxindole-1-N-t-butylcarboxamide

A mixture of 3-benzyloxycarbonyl-6-trifluoromethyl-4-azaoxindole-1-N-t-butylcarboxamide (1.10 g, 2.53 mmol), 10% palladium on characoal (300 mg) and ethanol (100 mL) was hydrogenated in a Parr shaker at 3 atmospheres pressure for 2 hr. The catalyst was removed by filtration of the mixture through celite and the solvent was evaporated to leave a gray solid (6-trifluoromethyl-4-azaoxindole-1-N-t-butylcarboxamide-3-carboxylic acid) (850 mg). This was taken up in ethanol (100 mL) and heated at reflux for 1.5 hr. After cooling to room temperature, the solvent was removed in vacuo. The residue was subjected to flash chromatography on silica gel using chloroform and then 10% methanol/chlorform as eluant. Fractions containing the desired product were combined and concentrated to leave the product as an off-white solid; 610 mg (80%).

F. 3-(2-Thenoyl)-6-trifluoromethyl-4-azaoxindole-1-N-t-butylcarboxamide

To a solution of 6-trifluoromethyl-4-azaoxindole-1-N-t-butylcarboxamide (350 mg, 1.16 mmol) and 4-dimethylaminopyridine (317 mg, 2.59 mmol) in dry dimethylformamide (5 mL) was added thiophene-2-carbonylchloride (0.14 mL, 1.3 mmol). The mixture was stirred at room temperature for 1.5 hr and then poured into ice/water. After adjustment of the pH to ca. 2 with 1N HCl solution, the resulting precipitate was collected by filtration (washing with water) and air dried. The material was then recrystallized twice from acetonitrile to afford a yellow solid, 160 mg (32%): mp>250° C.

$^1$H NM ($CDCl_3$): δ14.12 (br s, 1H), 9.18 (s, 1H), 8.74 (d, J=3 Hz, 1H), 8.52 (s, 1H), 8.14 (s, 1H), 7.94 (d, J=5 Hz, 1H), 7.25 (dd, J=3.5 Hz, 1H), 1.41 (s, 9H). MS m/e (relative percent) 411 (2), 312 (23), 228 (100), 111 (27). IR (KBr disc) 1725, 1675, 1645, 1605, 1535, 1520, 1500, 1415 $cm^{-1}$. Analysis calcd. for $C_{18}H_{16}O_3N_3F_3S$: C 52.55; H, 3.92; N 10.21. Found: C, 52.52; H 3.84; N 10.12.

EXAMPLE 8

3-(2-Furoyl)-6-trifluoromethyl-4-azaoxindole-1-N-t-butyl-carboxamide

The title compound was prepared from 6-trifluoromethyl-4-azaoxindole-1-N-t-butylcarboxamide (Example 7E) according to the procedure described in Example 7F, using 300 mg (1.0 mmol) 6-trifluoromethyl-4-azaoxindole-1-N-t-butylcarboxamide, 0.11 ml (1.1 mmol) 2-furoyl chloride, 244 mg (2.0 mmol) 4-N,N-dimethylaminopyridine and 10 mL DMF. The crude product was triturated with methanol, recrystallized from acetic acid and again triturated with methanol to afford the title compound. Yield: 230 mg (58%). M.p.>250° C.

$^1$H NMR (DMSO $d_6$) δ9.22 (s, 1H), 8.52 (d, J=1.7 Hz, 1H), 8.18–8.17 (m, 2H), 8.00 (d, J=1.7 Hz, 1H), 6.74–6.72 (m, 1H), 1.41 (s, 9H). MS m/e (relative percent) 395 (3), 296 (53), 228 (100). IR (KBr disc) 1720, 1670, 1640, 1615, 1540, 1515, 1460, 1425 $cm^{-1}$. Analysis calc'd For $C_{18}H_{16}F_3N_3O_4$ ⅓$H_2O$ C 54.07, H 4.16, N 10.51. Found: C 53.89, H 3.97, N 10.41.

EXAMPLE 9

5-Isopropoxy-3-(2-thenoyl)-4-azaoxindole-1-N-t-butyl-carboxamide

A. (3-Amino-6-isopropoxy-2-pyridyl)acetonitrile

To a stirred solution of potassium-t-butoxide (12.34 g, 110 mmol) in dry dimethylformamide (DMF) (30 mL) cooled at −10° C. under a nitrogen atmosphere was added dropwise a solution of (4-chlorophenoxy)acetonitrile (9.22 g, 55 mmol) and 2-isopropoxy-5-nitro pyridine (prepared according to the methodology of Friedman, et al., *J. Am. Chem. Soc.* 69, 1204 (1947)) (9.11 g, 50 mmol) in DMF (30 mL). The resulting purple solution was maintained at 0° to 10° C. for 1 hour. Aqueous hydrochloric acid was added (80 mL, 5% HCl) and the resulting mixture was allowed to warm to room temperature. The mixture was extracted twice with methylene chloride. The combined extracts were dried ($MgSO_4$) and concentrated in vacuo to leave an oil which was passed through a thick pad of silica gel, eluting with 1:1 methylene chloride/hexane. The filtrate was evaporated under reduced pressure and the residual oil containing the desired (6-isopropoxy-3-nitro-2-pyridyl) acetonitrile) was dissolved in a 6:1 mixture of ethanol and acetic acid (10 mL) to which was added 5% palladium/carbon (0.8 g). The mixture was hydrogenated on a Parr shaker at 3 atmospheres pressure for 5 hours. The catalyst was removed by filtration of the mixture through diatomaceous earth (Celite (trademark)) and The filtrate was concentrated in vacuo. The residual oil was taken up in water and the pH was adjusted to 10 by addition of sodium carbonate. The mixture was extracted twice with methylene chloride and the combined extracts were dried ($MgSO_4$) and concentrated. The residue was subjected to flash chromatography on silica gel eluting successively with 1:2 ether/hexane, 1:1 ether/hexane and ethyl acetate. Fractions containing the product eluted with ethyl acetate were combined and evaporated to provide (3-amino-6-isopropoxy-2-pyridyl)acetonitrile as an off-white solid (5.60 g, 59%); m.p. 83°–85° C.

B. 5-Isopropoxy-4-azaoxindole

A solution of (3-amino-6-isopropoxy-2-pyridyl) acetonitrile (4.5 g, 23.5 mmol) in 3N HCl solution was heated at 50°–55° C. overnight. After cooling to 0° C., the mixture was made basic by the slow addition of concentrated NaOH solution. The mixture was extracted twice with ethyl acetate and the combined ethyl acetate fractions were washed with brine, dried (MgSO$_4$) and concentrated to leave a solid. This was subjected to flash chromatography on silica gel eluting with 9:1 chloroform/methanol. Fractions containing the desired product, 5-isopropoxy-4-azaoxindole, were concentrated to leave a tan solid (1.0 g, 22%).

C. 5-Isopropoxy-3-(2-thenoyl)-4-azaoxindole

Pellets of sodium metal (250 mg, 11 mmole) were added to dry ethanol (10 mL) in a dry round-bottomed flask. When dissolution of the sodium was complete, solid 5-isopropoxy-4-azaoxindole (419 mg, 2.22 mmol) was added followed by ethyl-2-thiophene carboxylate (0.59 mL, 688 mg). The mixture was heated at reflux overnight and then cooled to room temperature. After pouring into ice/water, the mixture was acidified using 1N HCl solution and extracted with ethyl acetate. The combined ethyl acetate extracts were washed with brine, dried (MgSO$_4$) and concentrated in vacuo. The residue was subjected to flash chromatography on silica gel eluting successively with chloroform and 49:1 chlorform/methanol. All fractions containing the desired product were combined and concentrated. The residue was again subjected to flash chromatography on silica gel eluting with chloroform. Fractions containing only the desired product were combined and concentrated to give 5-isopropoxy-3-(2-thenoyl)-4-azaoxindole as a yellow gum (300 mg, 45%).

D. 5-Isopropoxy-3-(2-thenoyl)-4-azaoxindole-1-N-t-butyl-carboxamide

To a solution of 5-isopropoxy-3-(2-thenoyl)-4-azaoxindole-1-N-t-butyl carboxamide (300 mg, 1.0 mmol) in dry DMSO (7 mL) was added sequentially triethylamine (0.3 mL, 2.2 mmol) and t-butylisocyanate (0.17 mL, 1.5 mmol). The resulting mixture was heated in an oil bath at 80° C. for 4 hours. After cooling to room temperature, the solution was poured into ice/water and acidified using 1N HCl solution. The precipitated solid was collected by filtration and air dried. The material was dissolved in ether and the resulting solution was treated with activated charcoal. After filtration of the mixture through diatomaceous earth (Celite (trademark)), the filtrate was concentrated in vacuo to leave a yellow solid. The crude 5-isopropoxy-3-(2-thenoyl)-4-azaoxindole-1-N-t-butyl carboxamide was recrystallized from cyclohexane to afford the pure material as a bright yellow crystalline solid (105 mg, 26%); m.p. 160°–163° C.

$^1$H NMR (DMSO d$_6$): δ9.20 (br s, 1H), 8.87 (d, J=3 Hz, 1H), 8.43 (d, J=8.5 Hz, 1H), 7.90 (d, J=5 Hz, 1H), 7.23 (dd, J=3, 5 Hz, 1H), 6.71 (d, J=8.5 Hz, 1H), 4.90 (heptet, J=6 Hz, 1H), 1.40 (s, 9H), 1.38 (d, J=6H, 6H). MS m/e (relative percent) 401 (12), 302 (61), 176 (100), 148 (18), 111 (59). IR (KBr disc) 1703, 1654, 1624, 1604, 1547, 1518, 1472, 1421 cm$^{-1}$. Analysis calc'd for C$_{20}$H$_{23}$H$_3$O$_4$S: C 59.83, H 5.77, N 10.47. Found: C 59.59, H 5.62, N 10.46.

EXAMPLE 10

5-Phenylthio-3-(2-thenoyl)-6-azaoxindole-1-N-t-butylcarboxamide

A. t-Butyl (3-nitro-6-phenylthio-2-pyridyl)acetate

To a mechanically stirred slurry of pulverized sodium hydroxide (16.0 g, 400 mmol) in DMSO (75 mL) was added dropwise a solution of 2-fluoro-5-nitropyridine (prepared as described by Finger and Starr, *J. Am Chem. Soc.*, 81, 2674 (1959)) (5.7 g, 40 mmol) and t-butyl(phenylthio)acetate (9.0 g, 40 mmol) in DMSO (75 mL) while maintaining the temperature of the reaction mixture below 30° C. The mixture was allowed to stir at room temperature overnight and was then poured into ice/water. After adjustment of the pH to bout 2 with 1N HCl solution, the mixture was extracted with ethyl acetate. The combined organic extracts were washed with brine, dried (MgSO$_4$) and concentrated in vacuo. The oily residue was subjected to flash chromatography on silica gel using 2:1 chloroform/hexane as eluant. Fractions containing the desired product were combined and concentrated to leave a yellow solid which was triturated with ether to leave t-butyl (3-nitro-6-phenylthio-2-pyridyl) acetate (1.5 g, 11%), m.p. 104°–107°.

B. 5-Phenylthio-6-azaoxindole

A solution of t-butyl (3-nitro-6-phenylthio-2-pyridyl) acetate (1.04 g, 3.0 mmol) in glacial acetic acid containing iron powder (600 mg, 10.7 mmol) was heated at reflux for 5 hours. After cooling to room temperature, the mixture was poured into ice/water and extracted with chloroform. The combined chloroform extracts were washed with brine, dried (MgSO$_4$) and concentrated to leave 5-phenylthio-6-azaoxindole as a light yellow solid (560 mg, 77%); m.p. 186°–189° C.

C. 5-Phenylthio-3-(2-thenoyl)-6-azaoxindole

Pellets of sodium metal (264 mg, 11.5 mmol) were added to dry ethanol (10 mL) in a dry round-bottomed flask. When dissolution of the sodium was complete, a slurry of 5-phenylthio-6-azaoxindole (560 mg, 2.3 mmol) in ethanol (5 mL) was added. The mixture was warmed to 50° C. at which point ethyl-2-thiophene carboxylate (0.55 mL, 4.6 mmol) was added. The mixture was then heated at reflux for 30 hours. After cooling to room temperature, the mixture was poured into ice/water and the pH adjusted to 1 by addition of 6N HCl solution. The precipitated solid was collected by filtration, dried and subjected to flash chromatography on silica gel using 9:1 chloroform/methanol as eluant. Fractions containing the desired product, 5-phenylthio-3-(2-thenoyl)-6-azaoxindole were combined and evaporated under reduced pressure to leave a gold solid (620 mg, 76%); m.p. 248°–252° C. (dec).

D. 5-Phenylthio-3-(2-thenoyl)-6-azaoxindole-1-N-t-butyl-carboxamide

To a solution of 5-phenylthio-3-(2-thenoyl)-6-azaoxindole (255 mg, 0.72 mmol) in DMSO (5 mL) was added sequentially, triethylamine (0.2 mL, 1.4 mmol) and t-butyl isocyanate (0.12 mL, 1.1 mmol). The solution was heated at 85° C. overnight. After cooling, the mixture was poured into ice/water and the pH was adjusted to about 2.5 by addition of 1N HCl solution. The solid was collected by filtration, dried in the air and recrystallized from chloroform and the methanol/chloroform to yield 5-phenylthio-3-(2-thenoyl)-6-azaoxindole-1-N-t-butylcarboxamide (70 mg, 22%); m.p.>250°.

$^1$H NMR (DMSO d$_6$) δ9.885 (s, 1H), 8.95 (s, 1H), 8.52–8.50 (m, 1H), 7.92 (s, 1H), 7.64–7.62 (m, 1H), 7.42–7.30 (m, 5H), 7.12–7.07 (m, 1H), 1.39 (s, 9H). IR (KBr disc) 1706, 1619, 1587, 1554, 1465, 1427 cm$^{-1}$. Analysis calc'd for C$_{23}$H$_{21}$O$_3$N$_3$S$_2$ ⅓CHCl$_3$: C 57.04, H 4.38, N 8.55. Found: C 56.74, H 4.60, N 8.23.

EXAMPLE 11

6-Chloro-3-(2-thenoyl)-4-azaoxindole-1-N-t-butyl-carboxamide

The title compound was prepared from 6-chloro-3-(2-thenoyl)-4-azaoxindole (Example 2B) according to the procedure of Example 1C, using 5-chloro-3-(2-thenoyl)-4-azaoxindole (450 mg, 1.6 mmol), t-butyl isocyanate (0.78 ml, 2.4 mmol), triethylamine (0.49 ml, 3.5 mmol), and DMSO (10 ml). The crude product was recrystallized from methanol/chloroform. The yield after recrystallization was 330 mg (55%). MS m/e (relative percent) 379 (3), 377(10), 280 (24), 278 (71), 196 (40), 194 (100), 111 (20). IR (KBr disc) 1717, 1659, 1597, 1424 cm$^{-1}$. Analysis calc'd. for $C_{17}H_{16}ClN_3O_3S$: C 54.04, H 4.27, N 11.12; Found: C 53.64, H 4.14, N 10.99.

EXAMPLE 12

6-Chloro-3-(2-furoyl)-4-azaoxindole-1-N-t-butylcarboxamide

6-Chloro-3-(2-furoyl)-4-azaoxindole was first prepared according to the procedure of Example 2B, using 6-chloro-4-azaoxindole (1.0 g, 5.9 mmol), sodium (678 gm, 29.5 mmol) ethyl-2-furoate (1.65, 11.8 mmol) and ethanol (30 mL). The crude product was triturated with hot methanol. Yield: 825 mg (53%). M.p. 250° C.

The title compound was then prepared from 6-chloro-3-(2-furoyl)-4-azaoxindole according to the procedure of Example 1C, using 6-chloro-3-(2-furoyl))-4-azaoxindole (400 mg, 1.5 mmol), t-butyl isocyanate (0.26 mg, 2.2 mmol) and triethylamine (0.41 mm, 3.0 mmol). The reaction time was 4 hours. The crude product was recrystallized from chloroform. Yield: 190 mg (35%). Analysis calc'd for $C_{17}H_{16}ClN_3O_4$: C 56.44, H 4.46, N 11.61; found: C 56.17, H 4.26, N 11.20. M.p.>250° C.

EXAMPLE 13

6-Chloro-3-(3-furoyl)-4-azaoxindole-1-carboxamide

6-Chloro-3-(3-furoyl)-4-azaoxindole was first prepared according to the procedure of Example 2B, using 6-chloro-4-azaoxindole (1.5 g, 8.9 mmol), sodium (1 g, 44.5 mmol), ethyl-3-furoate (2.4 ml, 17.8 mmol), and ethanol (40 mL). The crude product was triturated with hot methanol. Yield: 1.0 g (43%) m.p. 250° C.

The title compound was then prepared from 6-chloro-3-(3-furoyl)-4-azaoxindole according to the procedure of Example 2C, using 6-chloro-3-(3-furoyl)-4-azaoxindole (500 mg, 1.9 mmol), N-chlorosulfonyl isocyanate (0.25 mL, 2.8 mmol), and acetonitrile (20 mL). The crude product was recrystallized from acetic acid. Yield: 175 mg (30%). Analysis calc'd for $C_{13}H_8ClN_3O_4$: C 51.08, H 2.64, N 13.75; found: C 51.04, H 2.41, N 13.46. M.p.>250°.

EXAMPLE 14

3-Benzoyl-6-chloro-4-azaoxindole-1-N-t-butylcarboxamide

3-Benzoyl-6-chloro-4-azaoxindole was first prepared according to the procedure of example 2B using 6-chloro-4-azaoxindole (1.5 g, 8.9 mmol), sodium (1 g, 44.5 mmol), ethyl benzoate (2.5 mL, 17.5 mmol), and ethanol (40 mL). The crude product was triturated with hot methanol. Yield: 1.2 g (49%).

The title compound was prepared from 3-benzoyl-6-chloro-4-azaoxindole according to the procedure of Example 1C, using 3-benzoyl-6-chloro-4-azaoxindole (500 mg, 1.83 mmol), t-butyl isocyanate (0.3 mL, 2.62 mmol), triethylamine (0.5 mL, 3.59 mmol), and DMSO (15 mL). The crude product was recrystallized from methanol/chloroform.

$^1$H NMR (DMSO-d$_6$): δ9.10 (s, 1H), 8.43 (d, J=1.4 Hz, 1H), 7.93 (d, J=1.4 Hz, 1H), 7.73 (d, J=7 Hz, 2H), 7.52–7.42 (m, 3H), 1.35 (s, 9H). Analysis calc'd for $C_{19}H_{18}ClN_3O_3$: C 61.38, H 4.88, N 11.30; found: C 61.19, H 4.51, N 10.99. M.p.>260° C.

EXAMPLE 15

6-Chloro-3-(2-furoyl)-4-azaoxindole-1-carboxamide

The title compound was prepared from 6-chloro-3-(2-furoyl)-4-azaoxindole (Example 12) according to the procedure of Example 2C, using 400 mg (1.5 mmol) 6-chloro-3-(2-furoyl)-4-azaoxindole, 0.19 ml (2.25 mmol) N-chlorosulfonyl isocyanate and 15 ml acetonitrile. The crude N-chlorosulfonyl carboxamide was hydrolysed by stirring in DMSO (5 ml), for 2 hours in a flask open to the air. The product was isolated by dilution with water filtration, and recrystallization from acetic acid. Yield: 160 mg (35%).

Analysis calc'd for $C_{13}H_8ClN_3O_4$: C 51.08, H 2.64, N 13.75; found: C 51.24, H 2.55, N 13.44. M.p.>250°.

EXAMPLE 16

6-Chloro-3-(4-chloro-2-thenoyl)-4-azaoxindole-1-N-t-butylcarboxamide

6-Chloro-3-(4-chloro-2-thenoyl)-4-azaoxindole was first prepared according to the procedure of Example 2B, using 6-chloro-4-azaoxindole (1.5 g, 8.9 mmol), sodium (1.0 g, 44.5 mmol), ethyl-4-chloro-2-thiophene carboxylate (3.3 g, 17.8 mmol), and ethanol (40 mL). Yield: 1.8 g (64%). M.p.>250° C.

The title compound was then prepared from 6-chloro-3-(4-chloro-2-thenoyl)-4-azaoxindole according to the procedure of Example 1C using 6-chloro-3-(4-chloro-2-thenoyl)-4-azaoxindole (900 mg, 2.8 mmol), t-butyl isocyanate (0.49 mL, 4.3 mmol), triethylamine (0.77 mL, 5.6 mmol), and DMSO (25 mL). The crude product was recrystallized from methanol. Yield: 140 mg (12%).

Analysis calc'd for $C_{17}H_5Cl_2N_3O_3S$: C 49.52, H 3.67, N 10.19; found: C 49.18, H 3.31, N 10.00. M.p.>250°.

EXAMPLE 17

6-Chloro-3-(3-furoyl)-4-azaoxindole-1-N-t-butylcarboxamide

The title compound was prepared from 6-chloro-3-(3-furoyl)-4-azaoxindole (Example 13) according to the procedure of Example 1C, using 6-chloro-3-(3-furoyl)-4-azaoxindole (500 mg, 1.9 mmol), t-butyl isocyanate (0.32 mL, 2.8 mmol), triethylamine (0.52 mL, 3.8 mmol), and DMSO (15 mL). The crude product was purified by successive chromatography on silica gel using chloroform as eluant, recrystallization from cyclohexane, flash chromatography on silica gel using 1:1 ethyl acetate/hexane and final recrystallization from cyclohexane. Yield: 160 mg (23%).

Analysis calc'd for $C_{17}H_{16}ClN_3O_4$: C 56.44, H 4.46, N 11.61; found: C 56.38, H 4.45, N 10.67. M.p. 250°.

EXAMPLE 18

3-Benzoyl-6-chloro-4-azaoxindole-1-carboxamide

The title compound was prepared from 3-benzoyl-6-chloro-4-azaoxindole (Example 14) according to the procedure of Example 2C, using 3-benzoyl-6-chloro-4- azaoxindole (500 mg, 1.83 mmol), N-chlorosulfonyl isocyanate (0.24 mL), 2.76 mmol) and acetonitrile (20 mL). The crude product was recrystallized from acetonitrile/chloroform. Yield: 121 mg (21%).

Analysis calc'd for $C_{15}H_{10}ClN_3O_3$: ¼ $CHCl_3$: C 53.01, H 2.98, N 12.16; found: C 53.14, H 2.78, N 11.92. M.P. 260°.

EXAMPLE 19

6-Chloro-3-(4-chloro-2-thenoyl)-4-azaoxindole-1-carboxamide

The title compound was prepared from 6-chloro-3-(4-chloro-2-thenoyl)-4-azaoxindole according to the procedure of Example 2C using 6-chloro-3-(4-chloro-2-thenoyl)-4-azaoxindole (850 mg, 2.7 mmol), N-chlorosulfonyl isocyanate (0.35 mL, 4.0 mmol) and acetonitrile (30 mL). The crude product was recrystallized from acetic acid. Yield: 280 mg (29%).

$^1$H NMR (DMSO-$d_6$): δ8.75 (d, J=1.2 Hz, 1H), 8.49 (br s, 1H), 8.38 (d, J=1.6 Hz, 1H), 7.92 (m, 3H). MS m/e (relative percent) 355 (5), 314 (8), 312 (14), 196 (21), 194 (72), 145 (30). IR (KBr disc) 1730, 1680, 1600, 1510, 1415 cm$^{-1}$. Analysis calc'd for $C_{13}H_7Cl_2N_3O_3S$: C 43.84, H 1.98, N 11.80; found: C 43.90, H 2.01, N 11.23. M.p.>250°.

EXAMPLE 20

6-Chloro-3-(4-methyl-2-thenoyl)-4-azaoxindole-1-N-t-butylcarboxamide

6-Chloro-3-(4-methyl-2-thenoyl)-4-azaoxindole was first prepared according to a variation of the procedure of Example 2B, using 6-chloro-4-azaoxindole (1.3 g, 7.71 mmol) sodium (1.75 g, 49.7 mmol), 4-methylthiophene-2-carbonyl chloride (1.93 g, 12.0 mmol) and ethanol (40 mL). Ethyl-4-methylthiophene-2-carboxylate was prepared in situ by addition of the acid chloride to the sodium ethoxide solution. The azaoxindole was added and the reaction carried out as in Example 1B. Yield: 1.64 g (46%) m.p.>250°.

The title compound was prepared from 6-chloro-3-(4-methyl-2-thenoyl)-4-azaoxindole according to the procedure of Example 1C, using 6-chloro-3-(4-methyl-2-thenoyl)-4-azaoxindole (470 mg, 1.6 mmol), t-butyl isocyanate (0.27 mL, 2.4 mmol), triethylamine (1.1 mL, 3.2 mmol), and DMSO (30 mL). The crude product was purified by successive flash chromatography on silica gel eluting with chloroform and recrystallization from chloroform/ethanol. Yield: 300 mg (48%). M.p.>250° C.

$^1$H NMR (DMSO $d_6$) δ9.19 (5, 1H), 8.57 (s, 1H), 8.42 (s, 1H), 7.91 (s, 1H), 7.50 (s, 1H), 2.27 (s, 3H), 1.41 (s, 9H). MS m/e (relative percent) 393 (1), 391 (3), 294 (10), 292 (27), 196 (33), 194 (100), 125 (23). IR (KBR disc) 1725, 1710, 1660, 1630, 1600, 1560, 1525, 1500 cm$^{-1}$. Analysis calc'd for $C_{18}H_{18}ClN_3O_3S$: C 55.17, H 4.63, N 10.72. Found: C 55.17, H 4.34, N 10.51.

EXAMPLE 21

6-Chloro-3-(2-thenoyl)-4-azaoxindole-1-N-phenylcarboxamide

The title compound was prepared from 6-chloro-3-(2-thenoyl)-4-azaoxindole (Example 2B) according to the procedure of Example 1B, using 6-chloro-3-(2-thenoyl)-4-azaoxindole (1.0 g, 3.6 mmol), phenyl isocyanate (0.58 mL, 5.4 mmol), triethylamine (1.0 mL, 7.2 mmol), and DMSO (35 mL). The crude product was recrystallized from acetic acid and then DMSO. Traces DMSO were removed by trituration with methanol. Yield: 515 mg (36%). M.p.>250°.

MS m/e (relative percent) 399 (8), 397 (23), 280 (37), 278 (100), 196 (28), 194 (86), 119 (93). IR (KBr disc) 1720, 1680, 1630, 1605, 1580, 1500, 1425, 1405 cm$^{-1}$. Analysis calc'd for $C_{19}H_{12}ClN_3O_3S$: C 57.36, H 3.04, N 10.56. Found: C 56.58, H 2.95, N 10.27.

EXAMPLE 22

5-Chloro-3-(2-thenoyl)-4-azaoxindole-1-carboxamide

The title compound was prepared from 5-chloro-3-(2-thenoyl)-4-azaoxindole (Example 1B), according to the procedure of Example 2C, using 5-chloro-3-(2-thenoyl)-4-azaoxindole (500 mg, 1.79 mmol), N-chlorosulfonyl isocyanate (0.18 mL, 2.15 mmol), and acetonitrile (15 mL). The crude N-chlorosulfonyl carboxamide was hydrolyzed by stirring in DMSO (1.5 mL) for 1 hour in a flask open to the air. The product was precipitated by addition of water and the precipitate was collected by filtration, and recrystallized from acetic acid. Yield: 36 mg (6%). MS m/e (relative percent) 323 (7), 321 (17), 280 (9), 278 (24), 196 (22), 194 (62), 170 (25), 168 (100). Exact mass calc'd for $C_{13}H_8 ClN_3O_3S$: 320.9975; found: 320.9977. IR (KBr disc) 1724, 1623, 1570, 1512, 1415 cm$^{-1}$. M.p. 222°–224° C.

EXAMPLE 23

5-Chloro-3-(2-furoyl)-4-azaoxindole-1-N-t-butylcarboxamide

5-Chloro-3-(2-furoyl)-4-azaoxindole was first prepared according to the procedure of Example 1B, using 5-chloro-4-azaoxindole (1.0 g, 5.9 mmol), sodium (0.68 g, 29.6 mmol), ethanol (30 mL) and ethyl-2-furoate (1.65 g, 11.8 mmol). Yield: 500 mg (33%). M.p.>250° C.

The title compound was then prepared according to the procedure of Example 1C, using 5-chloro-3-(2-furoyl)-4-azaoxindole (500 mg, 1.90 mmol), t-butyl isocyanate (0.33 mL, 2.9 mmol), triethylamine (0.53 mL, 3.8 mmol), and DMSO (10 mL). The crude product was recrystallized from methanol. Yield: 240 mg (35%). M.p. 194°–195° C.

$^1$H NMR (DMSO-$d_6$): δ8.96 (s, 1H), 8.38 (s, 1H), 8.35 (d, J=8.3 Hz, 1H), 8.06 (s, 1H), 7.24 (d, J=8.3 Hz, 1H), 6.80–6.78 (m, 1H), 1.40 (s, 9H). IR (KBr disc) 1725, 1590, 1569, 1541 cm$^{-1}$. MS m/e (relative percent) 361 (10), 262 (13), 196 (37), 194 (100), 95 (4). Analysis calc'd for $C_{17}H_{16}ClN_3O_4$: C 56.44, H, 4.46, N 11.61. Found: C 56.18, H 4.43, N 11.56.

EXAMPLE 24

5-Chloro-3-(2-furoyl)-4-azaoxindole-1-carboxamide

The title compound was prepared from 5-chloro-3-(2-furoyl)-4-azaoxindole (Example 23) according to the procedure of Example 2C, using 5-chloro-3-(2-furoyl)-4-azaoxindole (200 mg, 0.76 mmol), N-chlorosulfonyl isocyanate (0.10 mL, 1.1 mmol) and acetonitrile (8 mL). Hydrolysis of the N-chlorosulfonyl carboxamide was achieved by quenching the above reaction with water and allowing the mixture to stir at room temperature overnight. The product was collected by filtration and recrystallized from DMSO. Yield: 75 mg (32%).

FAB MS m/e 306. M.p. 248°–260° C.

EXAMPLE 25

5-Chloro-3-(2-thenoyl)-4-azaoxindole-1-N-phenylcarboxamide

The title compound was prepared from 5-chloro-3-(2-thenoyl)-4-azaoxindole (Example 1B) according to the procedure of Example 1C, using 5-chloro-3-(2-thenoyl)-4-azaoxindole (500 mg, 1.8 mmol), phenyl isocyanate (0.29 mL, 2.7 mmol), triethylamine (0.54 mL, 3.9 mmol), DMSO (10 mL). The crude product was recrystallized from ethyl acetate. Exact mass calc'd for $C_{19}H_{12}{}^{35}ClN_3S$: 397.0287; found: 397.0295. IR (KBr disc) 1728, 1622, 1603, 1582, 1563, 1412 cm$^{-1}$. Analysis calc'd for $C_{19}H_{12}ClN_3O_3S$: C 57.36, H 3.04, N 10.56; found: C 56.84, H 2.87, N 10.52. M.p. 226°–228° C.

EXAMPLE 26

5-Chloro-3-(2-thenoyl)-4-azaoxindole-1-N-cyclohexylcarboxamide

The title compound was prepared from 5-chloro-3-(2-thenoyl)-4-azaoxindole (Example 1B) according to the procedure of Example 1C, using 5-chloro-3-(2-thenoyl)-4-azaoxindole (560 mg, 2.0 mmol), cyclohexyl isocyanate (0.38 mL, 3.0 mmol), triethylamine (0.56 mL, 4.0 mmol), and DMSO (10 mL). The crude product was triturated with methanol and recrystallized from methanol/chloroform. Yield: 91 mg (11%).

M.P. 169°–170°. Analysis calc'd for $C_{19}H_{18}Cl_3O_3S$ ½$H_2O$: C 55.27, H 4.64, N 10.17. Found: C 55.17, H 4.34, N 9.87.

MS m/e (relative percent) 405 (1), 403 (3), 280 (22), 278 (56), 196 (33), 194 (100), 111 (14). IR (KBr disc) 1712, 1625, 1585, 1518, 1417 cm$^{-1}$.

EXAMPLE 27

5-Chloro-3-(4-chloro-2-thenoyl)-4-azaoxindole-1-N-t-butylcarboxamide

5-Chloro-3-(4-chloro-2-thenoyl)-4-azaoxindole was first prepared according to the procedure of Example 20, using 5-chloro-4-azaoxindole (1.0 g, 5.93 mmol), sodium (0.95 g, 41.3 mmol), ethanol (25 mL), and 4-chlorothiophene-2-carbonyl chloride (2.2 g, 11.3 mmol). Yield: 1.68 g (90%).

The title compound was then prepared from 5-chloro-3-(4-chloro-2-thenoyl)-4-azaoxindole according to the procedure of Example 1C, using 5-chloro-3-(4-chloro-2-thenoyl)-4-azaoxindole (0.75 g, (2.39 mmol), t-butyl isocyanate (0.4 mL, 3.5 mmol), triethylamine (0.65 mL, 4.7 mmol), and DMSO (20 mL). The crude product was purified by successive flash chromatography on silica gel using ethyl acetate as eluant and recrystallization from methanol/chloroform. Yield: 438 mg (44%).

Analysis calc'd for $C_{17}H_{15}Cl_2N_3O_3S$: C 49.53, H 3.67, N 10.19; found: C 49.58, H 3.39, N 9.94. M.p. 208°–209° C.

EXAMPLE 28

5-Chloro-3-(4-chloro-2-thenoyl)-4-azaoxindole-1-carboxamide

The title compound was prepared from 5-chloro-3-(4-chloro-2-thenoyl)-4-azaoxindole (Example 27) according to the procedure of Example 2C, using 5-chloro-3-(4-chloro-2-thenoyl)-4-azaoxindole (0.75 g, 2.39 mmol), N-chlorosulfonyl isocyanate (0.31 mL, 3.56 mmol), and acetonitrile (12 mL). Hydrolysis of the N-chlorosulfonyl carboxamide was achieved by stirring in DMSO (8 mL) for 4 hours at room temperature in a flask open to the air. The product was obtained by dilution of the mixture with water followed by filtration and recrystallized from acetic acid. Yield: 352 mg (41%).

Analysis calc'd for $C_{13}H_7Cl_2N_3O_3S$: C 43.84, H 1.98, N 11.80; found: C 43.52, H 1.93, N 11.52. M.p.>250° C.

EXAMPLE 29

5-Chloro-3-(2-thenoyl)-4-azaoxindole-1-N-(2,4-dichlorophenyl)carboxamide

The title compound was prepared from 5-chloro-3-(2-thenoyl)-4-azaoxindole (Example 1B) according to the procedure of example 1C, using 5-chloro-3-(2-thenoyl)-4-azaoxindole (580 mg, 2.08 mmol), triethylamine (0.58 mL, 4.15 mmol), 2,4-dichlorophenyl isocyanate (0.57 g, 3.1 mmol), and DMSO (10 mL). The crude product was recrystallized from methanol/chloroform. Yield: 231 mg (24%).

Analysis calc'd for $C_{19}H_{10}Cl_3N_3O_3S$: C 48.90, H 2.16, N 9.00; found: C 48.73, H 1.95, N 8.97. M.p. 244.5°–245° C.

EXAMPLE 30

5-Chloro-3-(4-methyl-2-thenoyl)-4-azaoxindole-1-N-t-butylcarboxamide

5-Chloro-3-(4-methyl-2-thenoyl)-4-azaoxindole was first prepared starting from 5-chloro-4-azaoxindole according to the procedure of Example 27, using 5-chloro-4-azaoxindole (1.45 g, 8.60 mmol), sodium (1.3 g, 56.5 mmol), and ethanol (40 mL) and 4-methylthiophene-2-carbonyl chloride (2.38 g, 14.8 mmol). Yield: 1.71 g (76%). Reaction time: overnight.

The title compound was then prepared from 5-chloro-3-(4-methyl-2-thenoyl)-4-azaoxindole according to the procedure of Example 1C, using 5-chloro-3-(4-methyl-2-thenoyl)-4-azaoxindole (0.8 g, 2.73 mmol), t-butyl isocyanate (0.5 mL, 4.36 mmol), triethylamine (0.8 mL, 5.74 mmol), and DMSO (25 mL). The crude product was first subjected to flash chromatography on silica using ethyl acetate as eluant. The material was subsequently recrystallized from methanol/methylene chloride. Yield: 600 mg (56%).

$^1$H NMR (DMSO-d$_6$): δ9.06 (s, 1H), 8.63 (s, 1H), 8.37 (d, J=8.2 Hz, 1H), 7.61 (s, 1H), 7.23 (d, J=8.2 Hz, 1H), 2.31 (s, 3H), 1.42 (s, 9H). MS m/e (relative percent) 393 (1), 391 (4), 294 (16), 292 (43), 196 (33), 194 (100), 125 (11). IR (KBr disc) 1720, 1670, 1585, 1540, 1415 cm$^{-1}$. Analysis calc'd for $C_{18}H_{18}ClN_3O_3S$: C 51.17, H 4.63, N 10.72; found: C 55.14, H 4.38, N 10.57. M.p. 167°–169° C.

EXAMPLE 31

5-Chloro-3-(4-methyl-2-thenoyl)-4-azaoxindole-1-carboxamide

The title compound was prepared from 5-chloro-3-(4-methyl-2-thenoyl)-4-azaoxindole (Example 30) according to the procedure of Example 2C, using 5-chloro-3-(4-methyl-2-thenoyl)-4-azaoxindole (0.90 g, 3.07 mmol), N-chlorosulfonyl isocyanate (0.40 mL, 4.60 mmol), and acetonitrile (15 mL). The crude N-chlorosulfonyl isocyanate was hydrolyzed by stirring in DMSO in a flask open to the air. The product was isolated by dilution with water and filtration, and was recrystallized from acetic acid. Yield: 190 mg (18%). M.P. 227°–228° C.

Analysis calc'd. for $C_{14}H_{10}ClN_3O_3S$: C 50.08, H 3.00, N 12.5.

Found: C 49.88, H 2.96, H 12.39.

$^1$H NMR (DMSO-d$_6$) δ: 8.71 (s, 1H), 8.46 (br s, 1H), 8.35 (d, J=8.5 Hz, 1H), 7.84 (br s, 1H), 7.61 (s, 1H), 7.24 (d, J=8.5

Hz, 1H), 2.31 (s, 3H). MS m/z (relative percent) 337 (33), 336 (42), 335 (100). IR (KBr disc) 1730, 1630, 1580, 1430 cm$^{-1}$.

EXAMPLE 32

3-Benzoyl-5-chloro-4-azaoxindole-1-N-t-butylcarboxamide

3-Benzoyl-5-chloro-4-azaoxindole was first prepared according to the procedure of Example 1B, using 5-chloro-4-azaoxindole (1.5 g, 8.9 mmol), sodium (1.0 g, 44.4 mmol), ethanol (40 mL) and ethyl benzoate (2.5 mL, 17.5 mmol). Yield 1.6 g (66%).

The title compound was then prepared from 3-benzoyl-5-chloro-4-azaoxindole according to the procedure of Example 1C, using 3-benzoyl-5-chloro-4-azaoxindole (800 mg, 2.93 mmol), triethylamine (0.8 mL, 5.74 mmol), t-butyl isocyanate (0.5 mL, 4.36 mmol) and DMSO (25 mL).

The crude product was purified by flash chromatography on silica gel using ethyl acetate as eluant, and recrystallized from hexanes. Yield: 320 mg (29%).

M.p. 107°–111° C. Analysis calc'd for $C_{19}H_{18}ClN_3O_3$: C 61.38, H 4.88, N 11.30. Found: C 62.00, H 5.11, N 10.75.

$^1$H NMR (DMSO-d$_6$) δ9.03 (s, 1H), 8.36 (d, J=8.2 Hz, 1H), 7.78 (d, J=6.9 Hz, 2H), 7.59–7.46 (m, 3H), 7.20 (d, J=8.2 Hz, 1H), 1.35 (s, 9H). MS m/e (relative percent) 373 (1), 371 (3), 274 (34), 272 (100), 194 (44), 105 (55). IR (KBr disc) 1730, 1720, 1590, 1550, 1455 cm$^{-1}$.

EXAMPLE 33

5-Chloro-3-(2-thenoyl)-4-azaoxindole-1-N-methylcarboxamide

The title compound was prepared from 5-chloro-3-(2-thenoyl)-4-azaoxindole (Example 1B) according to a variation of the procedure of Example 1C. The reaction was carried out at 55° C. using a dry-ice condenser to prevent loss of methyl isocyanate. Reaction time: 5 hours. The following amounts of reactants were used: 5-chloro-3-(2-thenoyl)-4-azaoxindole (560 mg, 2.0 mmol), methyl isocyanate (0.18 mL, 3.0 mmol), triethylamine (0.56 mL, 4.0 mmol) and DMSO (10 mL).

The crude product was recrystallized from methanol/chloroform. Yield: 151 mg (23%). M.p. 179°–180°.

$^1$H NMR (CDCl$_3$) δ8.98–8.94 (m, 2H), 8.45 (d, J=8.5 Hz, 1H), 7.70 (d, J=5 Hz, 1H), 7.22 (dd, J=3, 5 Hz, 1H), 7.02 (d, J=8.5 Hz, 1H), 3.01 (s, 0.5H), 2.99 (s, 0.5H).

Analysis calc'd for $C_{14}H_{10}ClN_3O_3S$ ½H$_2$O: C 47.88 H 3.21, N 12.18. Found: C 49.00, H 2.84, N 12.05. Exact mass calc'd for $C_{14}H_{10}$ $^{35}ClN_3O_3S$: 335.0121. Found: 335.0012.

EXAMPLE 34

5-Chloro-3-(3-furoyl)-4-azaoxindole-1-N-t-butylcarboxamide

5-Chloro-3-(3-furoyl)-4-azaoxindole was first prepared according to the procedure of Example 1B, using 5-chloro-4-azaoxindole (1.0 g, 5.9 mmol), sodium (6.82 mg, 29.6 mmol), ethyl-3-furoate (1.5 mL, 11.8 mmol) and ethanol (25 mL). Yield: 1.2 g (80%).

The title compound was prepared from 5-chloro-3-(3-furoyl)-4-azaoxindole according to the procedure of Example 1C, using 5-chloro-3-(3-furoyl)-4-azaoxindole (1.2 g, 4.5 mmol), t-butyl isocyanate (0.78 mL, 6.8 mmol), triethylamine (1.2 mL, 9.0 mmol) and DMSO (45 mL).

The crude product was subjected to flash chromatography on silica gel using 4:1 ethyl acetate/hexane as eluant. Fractions containing the desired product afforded a solid which was triturated with methanol and recrystallized from acetonitrile. Yield: 740 mg (76%). M.p. 182°–184° C.

$^1$H NMR (DMSO-d$_6$) δ9.13 (br s, 1H), 8.77 (br s, 1H), 8.32 (d, J=8.6 Hz, 1H), 7.86 (s, 1H), 7.25 (d, J=8.6 Hz, 1H), 7.12 (s, 1H), 1.40 (s, 9H). MS m/e (relative percent) 363 (5), 361 (16), 264 (34), 262 (100), 247 (6), 245 (19), 236 (17), 234 (41), 194 (24). IR (KBr disc) 1725, 1490, 1545 cm$^{-1}$. Analysis calc'd for $C_{17}H_{16}ClN_3O_4$: C 56.44, H 4.46, N 11.61. Found: C 56.33, H 4.17, N 11.68.

EXAMPLE 35

6-Fluoro-3-(2-thenoyl)-4-azaoxindole-1-carboxamide

The title compound was prepared from 6-fluoro-3-(2-thenoyl)-4-azaoxindole (Example 5) according to the procedure of Example 2C, using 6-fluoro-3-(2-thenoyl)-4-azaoxindole (419 mg, 1.60 mmol), N-chlorosulfonyl isocyanate (0.2 mL, 2.3 mmol), and acetonitrile (8 mL). Reaction time: 3 days. The crude N-chlorosulfonyl carboxamide was hydrolysed by stirring in DMSO in a flask open to the air, diluting with water, and collecting the product by filtration. The product was recrystallized from acetic acid. Yield: 210 mg (43%).

Analysis calc'd for $C_{13}H_8FN_3O_3S$: C 51.15, H 2.64, N 13.76; found: C 50.90, H 2.46, N 13.45. M.p. 265° C.

EXAMPLE 36

6-Fluoro-3-(4-methyl-2-thenoyl)-4-azaoxindole-1-N-t-butylcarboxamide

6-Fluoro-3-(4-methyl-2-thenoyl)-4-azaoxindole was first prepared according to the procedure of Example 20, using 6-fluoro-4-azaoxindole (1.0 g, 657 mmol), sodium (1.05 g, 45.6 mmol), ethanol (30 mL) and 4-methylthiophene-2-carbonyl chloride (1.86 g, 11.6 mmol). Yield: 1.17 g (64%).

The title compound was then prepared from 6-fluoro-3-(4-methyl-2-thenoyl)azaoxindole according to the procedure of Example 5E. After chromatography, the product was recrystallized from methanol. Yield: 234 mg (31%).

$^1$H NMR (DMSO-d$_6$): δ14.0 (br s, 1H), 9.24 (s, 1H), 8.60 (s, 1H), 8.45 (dd, J=2.3, 9.4 Hz 1H), 7.99–7.96 (m, 1H), 7.50 (s, 1H), 2.28 (s, 3H), 1.42 (s, 9H). MS m/e (relative percent) 375 (15), 276 (67), 178 (100), 125 (12). IR (KBr disc) 1720, 1670, 1610, 1560, 1530, 1425 cm$^{-1}$. Analysis calcd for $C_{18}H_{18}FN_3O_3S$: C 57.59, H 4.83, N 11.19; found: C 57.37, H 4.73, N 11.33 M.p. 275° C.

EXAMPLE 37

6-Fluoro-3-(4-methyl-2-thenoyl)-4-azaoxindole 1-carboxamide

The title compound was prepared from 6-fluoro-3-(4-methyl-2-thenoyl)-4-azaoxindole (Example 36) according to the procedure of Example 2C, using 6-fluoro-3-(4-methyl-2-thenoyl)-4-azaoxindole (614 mg, 2.22 mmol), N-chlorosulfonyl isocyanate (0.30 mL, 3.45 mmol) and acetonitrile (10 mL). The crude N-chlorosulfonyl carboxamide was hydrolysed by stirring in DMSO (4 mL) overnight in a flask open to the air. The product was isolated by dilution with water, filtration, and recrystallization from acetic acid. Yield: 249 mg (35%). M.p.>250°.

Analysis calc'd for $C_{14}H_{10}FN_3O_3S$: C 52.66, H 3.16, N 13.16. Found: C 52.16, H 3.00, N 13.03.

$^1$H NMR (DMSO-d$_6$) δ13.96 (br s, 1H), 8.64 (s, 1H), 8.60 (br s, 1H), 8.39 (dd, J=2.3, 9.5 Hz, 1H), 7.96 (dd, J=2.3, 3.5 Hz, 1H), 7.89 (br s, 1H), 7.49 (s, 1H), 2.26 (s, 3H). Ms m/e (relative percent) 319 (7), 276 (13), 178 (100), 125 (19). IR (KBr disc) 1725, 1610, 1590, 1510, 1430 cm$^{-1}$.

EXAMPLE 38

3-(2-Thenoyl)-6-azaoxindole-1-N-t-butylcarboxamide 3-(2-Thenoyl)-6-azaoxindole was first prepared according to the procedure of Example 1B, using 6-azaoxindole (2.8 g, 20.9 mmol), sodium (2.4 g, 104 mmol), ethanol (45 mL), and ethyl thiophene-2-carboxylate (55 mL, 40.9 mmol). Yield: 4.05 g (79%). M.p.>280° C.

The title compound was then prepared from 3-(2-thenoyl)-6-azaoxindole according to the procedure of Example 1C, using 3-(2-thenoyl)-4-azaoxindole (500 mg, 2.0 mmol), t-butyl isocyanate (0.35 mL, 3.0 mmol), triethylamine (0.6 mL, 4.4 mmol) and DMSO (10 mL).

The crude product was subjected to flash chromatography eluting with 9:1 chlorform/methanol. Fractions containing only the desired product were combined and concentrated to afford a solid which was recrystallized from acetone/methanol/chloroform. Yield: 390 mg (57%).

$^1$H NMR (DMSO-d$_6$): δ9.57 (s, 1H), 8.91 (s, 1H), 8.43 (d, J=3.5 Hz, 1H), 8.15 (d, J=6.4 Hz, 1H), 8.09 (d, J=6.4 Hz, 1H), 7.80 (d, J=5 Hz, 1H)), 7.17 (dd, J=3.5, 5 Hz, 1H), 1.40 (s, 9H). MS m/e (relative percent) 343 (0.4), 244 (6), 160 (27), 111 (9), 84 (100). IR (KBr disc) 1715, 1593, 1539, 1408 cm$^{-1}$. Analysis calc'd for $C_{17}H_{17}N_3O_3S$: C 59.46, H 4.99, N 12.24; found: C 58.99, H 4.85, N 12.10. M.p. 250°–252° C.

EXAMPLE 39

5-Chloro-3-(2-thenoyl)-6-azaoxindole-1-carboxamide

The title compound was prepared from 5-chloro-3-(2-thenoyl)-6-azaoxindole (Example 3C) according to the procedure of Example 2C, using 5-chloro-3-(2-thenoyl)-6-azaoxindole (140 mg, 0.5 mmol), N-chlorosulfonyl isocyanate (65 L, 0.75 mmol), and acetonitrile (5 mL). The crude N-chlorosulfonyl carboxamide was hydrolysed by stirring in DMSO for 2 hours in a flask open to the air. The product was precipitated by addition of water and was collected by filtration. The solid was recrystallized from methanol. Yield: 27 mg (17%).

$^1$H NMR (DMSO-d$_6$): δ8.73 (br s, 1H), 8.61 (s, 1H), 8.42 (d, J=4 Hz, 1H), 8.03 (s, 1H), 7.80 (d, J=5 Hz, 1H), 7.76 (br s, 1H),7.14 (dd, J=4, 5 Hz, 1H). FAB MS m/e 322. M.p. 252° C.

EXAMPLE 40

3-(2-Thenoyl)-7-azaoxindole-1-N-t-butylcarboxamide 3-(2-Thenoyl)-7-azaoxindole was first prepared according to the procedure of Example 1B, using 7-azaoxindole (1.5 g, 11.2 mmol), sodium (1.3 g, 56.5 mmol), ethanol (25 mL), and ethyl-thiophene-2-carboxylate (3 mL, 22.3 mmol). Yield: 2.54 g (93%).

The title compound was prepared from 3-(2-thenoyl)-7-azaoxindole according to the procedure of Example 1C, using 3-(2-thenoyl)-7-azaoxindole (500 mg, 2.0 mmol), t-butyl isocyanate (0.35 mL, 3.0 mmol), triethylamine (0.6 mL, 4.4 mmol) and DMSO (10 mL). The crude product was purified by flash chromatography on silica gel using 9:1 chloroform/methanol and recrystallized from methanol/chlorform. Yield: 70 mg (25%).

$^1$H NMR (DMSO-d$_6$): δ9.34 (s, 1H), 8.81 (d, J=3.5 Hz, 1H), 8.54 (d, J=8.0 Hz, 1H), 7.91–7.87 (m, 2H), 7.25–7.18 (m, 2H), 1.41 (s, 9H). MS m/e (relative percent) 343 (35), 244 (81), 160 (100), 111 (9). IR (KBr disc) 1718, 1654, 1629, 1607, 1554, 1534, 1497, 1433 cm$^{-1}$. Analysis calc'd for $C_{17}H_{17}N_3O_3S$: C 59.46, H 4.99, N 12.24; found: C 59.24, H 4.77, N 12.14. M.p.>250° C.

EXAMPLE 41

5,6-Dichloro-3-(2-thenoyl)-4-azaoxindole-1-carboxamide

The title compound was prepared from 5,6-dichloro-3-(2-thenoyl)-4-azaoxindole (Example 6B) according to the procedure of Example 2C, using 5,6-dichloro-3-(2-thenoyl)-4-azaoxindole (194 mg, 0.62 mmol), N-chlorosulfonyl isocyanate (81 L, 0.93 mmol) acetonitrile (10 mL), and a temperature of 50° C. The crude N-chlorosulfonyl carboxamide was hydrolysed by stirring in DMSO in a flask open to the air. After dilution with water, the solid was collected by filtration and recrystallized from acetic acid. Yield: 129 mg (58%).

$^1$H NMR (DMSO-d$_6$): δ8.66 (d, J=3.5 Hz, 1H), 8.58 (br s, 1H), 8.36 (s, 1H), 7.95 (d, J=5 Hz, 1H), 7.78 (br s, 1H), 7.26 (dd, J=3.5, 5 Hz, 1H). IR (DMSO) 1710, 1550, 1515, 1455 cm$^{-1}$. Analysis calc'd for $C_{13}H_7Cl_2N_3O_3S$: C 43.84, H 1.98, N 11.80; found: C 43.65, H 1.87, N 11.68. M.p. 237°–239.5° C.

EXAMPLE 42

3-(2-Thenoyl)-6-azaoxindole-1-carboxamide

The title compound was prepared from 3-(2-thenoyl)-6-azaoxindole (Example 38) according to the procedure of Example 2C, using 3-(2-thenoyl)-6-azaoxindole (3.09 g, 12.6 mmol), N-chlorosulfonyl isocyanate (1.2 mL, 13.8 mmol) and acetonitrile (60 mL). Reaction time: 3½ hours.

The crude N-chlorosulfonyl carboxamide was hydrolysed by stirring in DMSO (30 mL) overnight in a flask open to the air. After dilution with water, the solid was collected by filtration and dried. The solid was then recrystallized twice from acetic acid and once from methyl ethyl ketone. Yield: 163 mg (5%). M.p. 213°–215° C.

$^1$H NMR (DMSO-d$_6$) δ8.86 (br s, 2H), 8.45 (d, J=3.6 Hz, 1H), 8.16–8.09 (m, 2H), 8.80 (d, J=4.3 Hz, 1H), 7.76 (br s, 1H), 7.16 (dd, J=3.6, 4.3 Hz, 1H). IR (KBr disc) 1733, 1708, 1630, 1559, 1517, 1479, 1418 cm$^{-1}$. Analysis calc'd for $C_{13}H_9N_3O_3S$: C 54.35, H 3.16, N 14.63. Found: C 54.04, H 3.24, N 14.16.

EXAMPLE 43

3-Phenylacetyl-6-azaoxindole-1-carboxamide

3-Phenylacetyl-6-azaoxindole was first prepared from 6-azaoxindole according to the procedure of Example 1B, using 6-azaoxindole (1 g, 7.4 mmol), sodium (257 mg, 11.2 mmol), ethylphenylacetate (2.3 mL, 14.9 mmol) and ethanol (30 mL). Reaction time: 4½ hours. Workup of the reaction involved pouring the mixture into ice/water and adjusting the pH of the mixture to about 6. The product was collected by filtration and washed with ethyl acetate. Yield: 1.23 g (66%). M.P. 250°.

The title compound was prepared from 3-phenylacetyl-6-azaoxindole according to the procedure of Example 2C, using 3-phenylacetyl-6-azaoxindole (1.0 g, 3.9 mmol), N-chlorosulfonyl isocyanate (0.41 mL, 4.7 mmol) and acetonitrile (40 mL). Reaction time: 4 hours. The crude N-chlorosulfonyl carboxamide was hydrolysed by stirring in DMSO (6 mL) for 1 hour in a flask open to the air. After dilution with water, the product was collected by filtration, dried, and recrystallized from acetic acid. Yield: 172 mg (15%). M.p. 131°–133° C. (dec.).

$^1$H NMR (DMSO-$d_6$) $\delta$13.28 (s, 1H), 8.86 (br s, 1H), 8.80–8.78 (m, 1H), 8.16 (br s, 2H), 7.74 (br s, 1H), 7.26–7.12 (m, 5H), 4.21 (s, 2H). MS m/e (relative percent) 252 (30), 161 (100). FAB MS Exact mass calc'd for $C_{16}H_{14}N_3O_3$ (M+1): 296.1035. Found: 296.1021.

EXAMPLE 44

5-Isopropoxy-3-(2-thenoyl)-4-azaoxindole-1-carboxamide

The title compound was prepared from 5-isopropoxy-3-(2-thenoyl)-4-azaoxindole (Example 9C) according to the procedure of Example 2C, using 5-isopropoxy-3-(2-thenoyl)-4-azaoxindole (70 mg, 0.23 mmol), N-chlorosulfonyl isocyanate (25 L, 0.29 mmol) and acetonitrile (1.5 mL). Reaction time: 4 hours. The crude N-chlorosulfonyl carboxamide was hydrolysed by stirring in chloroform for 3 days. After removal of the solvent in vacuo, the product was purified by flash chromatography on silica gel using 2:1 ethyl acetate/hexane as eluant and trituration with ether. Yield: 30 mg (37%). M.p. 194°–196° C.

$^1$H NMR (DMSO-$d_6$) $\delta$13.04 (s, 1H), 9.08 (br s, 1H), 8.99–8.98 (m, 1H), 8.48 (d, J=8.6 Hz, 1H), 7.62–7.60 (m, 1H), 7.19–7.16 (m, 1H), 6.26 (d, J=8.6 Hz, 1H), 5.29 (br s, 1H), 4.74 (heptet, J=6.4 Hz, 1H), 1.42 (d, J=6.4 Hz, 1H). IR (KBr disc) 1720, 1607, 1565 cm$^{-1}$. FAB MS Exact mass calc'd for $C_{16}H_{16}H_3O_4S$ (M+1): 346.0862. Found: 346.0844.

EXAMPLE 45

3-(4-Chloro-2-thenoyl)-5-azaoxindole-1-N-t-butylcarboxamide 3-(4-Chloro-2-thenoyl)-5-azaoxindole was first prepared from 5-azaoxindole (Example 4B) according to the procedure of Example 20, using 5-azaoxindole (1.0 g, 7.45 mmol), sodium (1.21 g, 52.6 mmol), 4-chlorothiophene-2-carbonyl chloride (2.72 g, 15.0 mmol) and ethanol (40 mL). Reaction time: 3 days. The crude product was triturated with methanol. Yield: 427 mg (21%). M.p 250° C.

The title compound was then prepared from 3-(4-chloro-2-thenoyl)-5-azaoxindole according to the procedure of Example 1C, using 3-(4-chloro-2-thenoyl)-5-azaoxindole (427 mg, 1.53 mmol), t-butyl isocyanate (0.26 mL, 2.3 mmol), triethylamine (0.43 mL, 3.1 mmol) and DMSO (10 mL). Reaction time: overnight. The crude product was purified by successive flash chromatography using ethyl acetate as eluant and recrystallization from acetonitrile. Yield: 172 mg (30%). M.p. 250° C.

$^1$H NMR (DMSO-$d_6$) $\delta$9.72 (s, 1H), 9.19 (s, 1H), 8.73 (s, 1H), 8.44 (d, J=7 Hz, 1H), 8.31 (d, J=7 Hz, 1H), 7.81 (s, 1H), 1.43 (s, 9H). Analysis calc'd for $C_{17}H_{16}Cl_3N_3O_3S$: C 54.04, H 4.27, N 11.12. Found: C 53.76, H 3.93, N 10.98.

EXAMPLE 46

3-(2-Thenoyl)-5-azaoxindole-1-carboxamide

The title compound was prepared from 3-(2-thenoyl)-4-azaoxindole (Example 4C) according to the procedure of Example 2C, using 3-(2-thenoyl)-5-azaoxindole (500 mg, 2.0 mmol), N-chlorosulfonyl isocyanate (0.26, 3.0 mmol), and acetonitrile (15 mL). Reaction time: 2.25 hours. The crude N-chlorosulfonyl carboxamide was hydrolysed by stirring in DMSO (1.5 mL) for 1.5 hours in a flask open to the air. Ether was added to give a two phase mixture followed by methanol, which gave a homogenous solution. On standing for a brief period, a green precipitate formed which was removed by filtration. The filtrate was allowed to stand overnight, during which time the product crystallized from the solution. This was collected by filtration. Yield: 39 mg (7%). M.p. 250°.

$^1$H NMR 14.21 (br s, 1H), 9.15 (s, 1H), 9.12 (br s, 1H), 8.68 (d, J=4 Hz, 1H), 8.37 (d, J=7 Hz, 1H), 8.24 (d, J=7H, 1H), 7.85 (br s, 1H), 7.72 (d, J=4.5 Hz, 1H), 7.14 (dd, J=4, 4.5 Hz, 1H). IR (KBr disc) 1741, 1476, 1433 cm$^{-1}$. FAB MS Exact mass calc'd for $C_{13}H_{10}N_3O_3S$ (M+1): 288.0443. Found: 288.0439.

EXAMPLE 47

Acetyl Prodrug of 6-Chloro-3-(2-thenoyl)-4-azaoxindole-1-carboxamide

To a suspension of 6-chloro-3-(2-thenoyl)-4-azaoxindole-1-carboxamide (500 mg, 1.55 mmol) in tetrahydrofuran (THF) (60 mL) was added sequentially triethylamine (0.4 mL, 2.87 mmol) and acetyl chloride (0.2 mL, 2.81 mmol). The mixture was stirred overnight at room temperature. Additional triethylamine (0.4 mL, 2.87 mmol) and acetyl chloride (0.2 mL, 2.81 mmol) were added. After stirring at room temperature for an additional 3 days, the mixture was filtered to collect the product. The product was washed sequentially with chloroform, water and methanol leaving a yellow solid (390 mg, 69%). A second crop of product was obtained from the filtrate by filtration, washing with chloroform (109 mg, 19%). The product samples were combined and recrystallized from chloroform, yielding a yellow solid (289 mg, 51%). M.p.>250° C.

$^1$H NMR (DMSO-$d_6$) $\delta$8.51 (d, J=4 Hz, 1H), 8.43 (d, J=2 Hz, 1H), 8.36 (d, J=2 Hz, 1H), 8.23 (d, J=5 Hz, 1H), 8.05 (br s, 2H), 7.37 (dd, J=4, 5 Hz, 1H). Acetyl $CH_3$ peak obscured by DMSO absorption at 2.50. Analysis calc'd for $C_{15}H_{10}ClN_3O_4S$: C 49.53 H 2.77, N 11.55. Found: C 49.23, H 2.53, N 11.52.

EXAMPLE 48

5-Chloro-3-(2-thenoyl)-4-azaoxindole-1-N-ethylcarboxamide

The title compound was prepared from 5-chloro-3-(2-thenoyl)-4-azaoxindole (Example 1B) according to the procedure of Example 1C, using 5-chloro-3-(2-thenoyl)-4-azaoxindole (1.25 g, 4.49 mmol), triethylamine (3.2 mL, 23 mmol), ethyl isocyanate (1.77 mL, 22.4 mmol) and dimethylsulfoxide (DMSO) (30 mL). The reaction time was 6 hours. The crude product was first triturated with hexane and then recrystallized from the same solvent. Yield: 1.09 g (70%).

Analysis calc'd for $C_{15}H_{12}ClN_3O_3S$: C 51.51, H 3.46, N 12.01. Found: C 51.56, H 3.21, N 11.90. M.p. 153°–154° C.

$^1$H NMR (CDCl$_3$) $\delta$9.04 (br s, 1H), 9.01 (dd, J=1, 4 Hz, 1H), 8.47 (d, J=8.2 Hz, 1H), 7.71 (dd, J=1, 4.9 Hz, 1H), 7.22

(dd, J=4, 4.9 Hz, 1 Hz), 7.03 (d, J=8.2 Hz, 1H), 3.51–3.41 (m, 2H), 1.28 (t, J=7.3 Hz, 3H).

IR (KBr disc) 1720, 1605, 1585, 1540, 1415 cm$^{-1}$. MS m/e (relative percent) 351(2), 349(5), 280(10), 278(29), 196(32), 194(100), 111(26).

EXAMPLE 49

5-Chloro-3-(2-thenoyl)-4-azaoxindole-1-N-isopropylcarboxamide

The title compound was prepared from 5-chloro-3-(2-thenoyl)-4-azaoxindole (Example 1B) according to the procedure of Example 1C, using 5-chloro-3-(2-thenoyl)-4-azaoxindole (1.25 g, 4.49 mmol), triethylamine (3.2 mL, 23 mmol), isopropyl isocyanate (2.2 mL, 22.4 mmol) and DMSO (30 mL). The reaction time was 6 hours. The crude product was recrystallized from hexane. Yield: 1.30 g (80%).

Analysis calc'd for $C_{16}H_{14}ClN_3O_3S$: C 52.82, H 3.88, N 11.55. Found: C 52.93, H 3.65, N 11.31. M.p. 163°–165° C.

$^1$H NMR (CDCl$_3$) δ9.02 (dd, J=1, 4 Hz, 1H), 8.96 (br d, 1H), 8.46(d, J=8.3 Hz, 1H), 7.71 (dd, J=1, 5 Hz, 1H), 7.22 (J=4, 5 Hz, 1H), 7.02 (d, J=8.3 Hz, 1H), 4.19–4.08 (m, 1H), 1.30 (d, J=6.6 Hz, 6H).

IR (KBr disc) 1710, 1605, 1585, 1540, 1520, 1420 cm$^{-1}$. MS m/e (relative percent) 365(3), 363(14), 280(17), 278 (45), 196(32), 194(100), 111(18).

EXAMPLE 50

3-Benzoyl-5-chloro-4-azaoxindole-1-carboxamide

The title compound was prepared from 3-benzoyl-5-chloro-4-azaoxindole (Example 32) according to the procedure of Example 25, using 3-benzoyl-5-chloro-4-azaoxindole (2.73 g, 10.0 mmol), N-chlorosulfonyl isocyanate (1.3 mL, 15 mmol) and acetonitrile (80 mL). The reaction time was 20 hours. The crude N-chlorosulfonyl carboxamide was hydrolyzed by stirring in DMSO (15 mL) for 20 hours. The crude product was recrystallized from acetic acid and washed with methanol. Yield: 0.36 g (11%).

Analysis calc'd for $C_{15}H_{10}ClN_3O_3$ ¼ $H_2O$: C 56.26, H 3.30, N 13.12. Found: C 56.26, H 2.92, N 13.25. M.p. 220° C.

$^1$H NMR (DMSO-d$_6$) δ8.41 (br s, 1H), 8.33 (d, J=8.3 Hz, 1H), 7.80 (d, J=7.3 Hz, 2H), 7.72 (br s, 1H), 7.58–7.45 (m, 3H), 7.20 (d, J=8.3 Hz, 1H).

IR (KBr disc) 1750, 1660, 1620, 1600, 1590, 1575, 1390 cm$^{-1}$.

EXAMPLE 51

5,6-Dichloro-3-(2-furoyl)-4-azaoxindole-1-N-t-butyl carboxamide 5,6-Dichloro-3-(2-furoyl)-4-azaoxindole was first prepared according to the procedure of Example 1B, using 5,6-dichloro-4-azaoxindole (763 mg, 3.76 mmol), sodium (0.43 g, 18.8 mmol), ethyl-2-furoate (1.05 g, 7.5 mmol) and ethanol (25 mL). Yield: 0.98 g (88%).

The title compound was prepared from 5,6-dichloro-3-(2-furoyl)-4-azaoxindole according to the procedure of Example 1C, using 5,6-dichloro-3-(2-furoyl)-4-azaoxindole (721 mg, 2.43 mmol), triethylamine (1.8 mL, 15.4 mmol), t-butyl isocyanate (1.4 mL, 12.3 mmol) and DMSO (20 mL). The reaction time was 22 hours. The crude product was triturated with methanol and recrystallized from hexane. Yield: 218 mg (23%).

Analysis calc'd for $C_{17}H_{15}Cl_2N_3O_4$: C 51.53, H 3.82, N 10.60. Found: C 51.70, H 3.81, N 10.57. M.p. 205°–206° C.

$^1$H NMR (DMSO-d$_6$) δ9.37 (br s, 1H), 8.32 (s, 1H), 7.91 (s, 1H), 7.85 (d, J=3.7 Hz, 1H), 6.69 (d, J=3.7 Hz, 1H), 1.38 (s, 9H).

IR (KBr disc) 1730, 1620, 1605, 1590, 1555, 1535 cm$^{-1}$. MS m/e (relative percent) 397(0.5), 395(2), 298(21), 296 (33), 230(62), 228(100), 95(40).

EXAMPLE 52

5-Chloro-3-(2-furoyl)-4-azaoxindole-1-N-(1-hydroxy-2-methyl)prop-2-yl carboxamide A) 2-Amino-1-benzyloxy-2-methylpropane A solution of 2-amino-2-methyl-1-propanol (7.1 mmol) in tetrahydrofuran (THF) (25 mL) was added dropwise to a slurry of 60% sodium hydroxide/oil (3 g, 75 mmol) in THF (75 mL). The mixture was stirred at room temperature for 1 hour and then cooled in an ice bath. A solution of benzyl bromide (5.9 mL, 50 mmol) was added dropwise. After stirring for 2 hours at 0° C., the reaction mixture was poured into ice/water and extracted with ethyl acetate. The organic phase was washed with brine, dried (MgSO$_4$) and concentrated to an oil which was subjected to flash chromatography on silica gel eluting with 5% methanol/chloroform. Fractions containing the desired product were combined and concentrated to yield an oil. Yield: 4.2 g (47%).

B) (1-Benzyloxy-2-methyl)prop-2-ylisocyanate

To an ice cooled solution of 2-amino-1-benzyloxy-2-methylpropane (2.1 g, 10 mmol) and triethylamine (4.5 mL, 32 mmol) in methylene chloride (50 mL) was added triphosgene (989 mg, 3.3 mmol) in three portions. The reaction mixture was stirred at 0° C. for 0.25 hour and then at room temperature for 4 hours. Volatiles were removed in vacuo and the resulting residue was triturated with ether to leave the desired product as an oil. Yield: 1.9 g (95%).

C) 5-Chloro-3-(2-furoyl)-4-azaoxindole-1-N-(1-benzyloxy-2-methyl)prop-2-ylcarboxamide The title compound was prepared from 5-chloro-3-(2-furoyl)-4-azaoxindole (Example 23) according to the procedure of Example 1C, using 5-chloro-3-(2-furoyl)-4-azaoxindole (1.90 g, 7.2 mmol), triethylamine (2.8 mL, 21 mmol), (1-benzyloxy-2-methyl)prop-2-ylisocyanate (2.2 g, 10.7 mmol) and DMSO (75 mL). The reaction was run overnight. The crude product was purified by flash chromatography on silica gel eluting with chloroform. Fractions containing the desired product were combined and concentrated to leave a yellow oil. Yield: 2.2 g (65%).

D) 5-Chloro-3-(2-furoyl)-4-azaoxindole-1-N-(1-hydroxy-2-methyl)prop-2-ylcarboxamide To an ice cooled solution of 5-chloro-3-(2-furoyl)-4-azaoxindole-1-N-(1-benzyloxy-2-methyl)prop-2-ylcarboxamide (1.0 g, 2.1 mmol) in methylene chloride (25 mL) was added dropwise a 1M solution of borontribromide (BBr$_3$) in methylene chloride (3 mL, 3 mmol). The reaction mixture was stirred at 0° C. for 2 hours, after which an additional portion of 1M BBr$_3$ in methylene chloride (0.5 mL, 0.5 mmol) was added. After another 1 hour at 0° C., the mixture was poured into ice/water and extracted with ethyl acetate. The organic phase was washed with brine, dried (MgSO$_4$) and concentrated to leave a yellow solid which was first triturated and then recrystallized from methanol. Yield: 552 mg (70%).

Analysis calc'd for $C_{17}H_{16}ClN_3O_5$: C 54.05, H 4.27, N 11.12. Found: C 53.82, H 4.05, N 10,92. M.p. 185°–186° C.

$^1$H NMR (CDCl$_3$) δ9.3 (br s, 1H), 8.49 (dd, J=1.3, 3.6 Hz, 1H), 8.38 (d, J=8.2 Hz, 1H), 7.70 (dd, J=1.3, 1.6 Hz, 1H), 6.98 (d, J=8.2 Hz, 1H), 6.61 (dd, J=1.6, 3.6 Hz, 1H), 3.73 (br s, 1H), 3.71 (s, 2H), 1.41 (s, 6H).

IR (KBr disc) 1730, 1720, 1665, 1630, 1595, 1540, 1460, 1445, 1420 cm$^{-1}$. MS m/e (relative percent) 380 (1), 379(3), 378(5), 377(9), 265(18), 264(50), 263(53), 262(100), 197 (12), 196(60), 195(33), 194(97), 95(25).

EXAMPLE 53

5-Chloro-1-ethyl-3-(2-thenoyl)-7-azaoxindole

A) 1-Ethyl-7-azaindole 10 grams (0.0846 moles) of 7-azaindole (Aldrich (trademark)) were dissolved in 200 mL of reagent grade acetone at room temperature and treated with 10 grams (0.178 moles) of powdered KOH. After~2–3 minutes, 67 mL (0.846 moles) of ethyl iodide was added over a period of 5–10 minutes and the reaction mixture was stirred at room temperature for 30–40 minutes. Thin layer chromatography (TLC) using 95% methylene chloride/5% ethyl acetate showed complete consumption of the starting material and formation of a single less polar product. The reaction mixture was concentrated in vacuo and the residue was partitioned between water and methylene chloride (350 mL). The organic layer was separated and washed with water and brine and dried (sodium sulfate). Concentration of the organic extract in vacuo gave a yellow-brown oil which was purified on a silica gel column eluting with methylene chloride/ethyl acetate (95%/5%). A total of 11.15 grams (90%) of pure final product (light yellow oil) was obtained.

60 MgHz $^1$H NMR (CDCl$_3$) δ: 1.35–1.65 (t, 3H); 4.20–4.60 (q, 2H); 6.35–8.45 (m, 5H).

B) 3,3-Dibromo-1-ethyl-7-azaoxindole

To a solution of 1-ethyl-7-azaindole (5.4 g, 34 mmol) in t-butanol (200 mL) at 30° C. were added, in portions, pyridinium bromide perbromide (27.2 g, 85 mmol). The reaction mixture was stirred at room temperature overnight and then poured into ice/water. After stirring for 0.5 hours, the mixture was extracted with ethyl acetate. The organic extract was washed with water, dried (magnesium sulfate) and concentrated to leave a brown oil. This was chromatographed on a column of silica gel eluting with chloroform. Fractions containing only the desired product were combined and concentrated in vacuo to leave a yellow oil, 5.30 g (49%).

C) 5-Chloro-3,3-dibromo-1-ethyl-7-azaoxindole

A solution of 3,3-dibromo-1-ethyl-7-azaoxindole (5.3 g, 16.5 mmol) in N,N-dimethylformamide (DMF) in a three-neck flask fitted with a dry ice condenser was cooled to 0° C. In an ice bath. Chlorine gas was bubbled through the solution for 4 minutes to achieve saturation. The reaction mixture was stirred at 0° C. for 2 hours and then poured into ice/water. After stirring for 0.5 hours, the mixture was extracted with ethyl acetate. The organic extract was washed with water, dried over magnesium sulfate, and concentrated to leave a yellow oil. This was chromatographed on a column of silica gel eluting with ethyl acetate. Fractions containing the desired product were combined and concentrated in vacuo to afford a yellow solid, 4.69 g (80%).

D) 5-Chloro-1-ethyl-7-azaoxindole

To a solution of 5-chloro-3,3-dibromo-1-ethyl-7-azaoxindole (4.60 g, 13.0 mmol) in glacial acetic acid (75 mL) was added, in portions, zinc powder (2.5 g, 39 mmol). An exothermic reaction took place immediately, however, stirring at room temperature was continued for 1 hour. The mixture was poured into ice/water and then extracted with ethyl acetate. The organic extract was washed with water, dried over magnesium sulfate and evaporated to leave an oil which was chromatographed on a column of silica gel eluting with chloroform. Fractions containing the desired product were combined and concentrated in vacuo to afford an off-white solid, 1.70 g (68%). M.p. 78°–82° C.

E) 5-Chloro-1-ethyl-3-(2-thenoyl)-7-azaoxindole

To a solution of 5-chloro-1-ethyl-7-azaoxindole (400 mg, 2.03 mmol) and 4-dimethylaminopyridine (537 mg, 4.4 mmol) in DMF (10 mL) at 0° C. was added thiophene-2-carbonyl chloride (0.24 mL, 2.24 mmol). The reaction mixture was stirred at room temperature for 2 hours and then poured into ice/water. The mixture was extracted with ethyl acetate. The organic layer was washed with water and brine, dried (magnesium sulfate) and concentrated in vacuo. The residue was chromatographed on a column of silica gel eluting with chloroform. Fractions containing only the desired product were combined and concentrated to afford the title compound as a solid which was recrystallized from hexanes. The yield of recrystallized material was 29 mg (50%).

M.p. 111°–112° C. Analysis calc'd for $C_{14}H_{11}ClN_2O_2S$: C 54.82, H 3.61, N 9.13. Found: C 54.45, H 3.34, N 8.80. MS m/z (relative percent) 308 (6), 306 (19), 224 (32), 222 (100), 209 (8), 207 (24), 196 (24), 194 (77), 111 (77).

EXAMPLE 54

5-Chloro-1-ethyl-3-(2-furoyl)-7-azaoxindole

The title compound was prepared from 5-chloro-1-ethyl-7-azaoxindole (Example 53D) according to the procedure of Example 53E, using 5-chloro-1-ethyl-7-azaoxindole (405 mg, 2.06 mmol), 4-dimethylaminopyridine (500 mg, 4.09 mmol), 2-furoyl chloride (0.22 mL, 2.23 mmol) and DMF (10 mL). The solid product obtained following chromatography was recrystallized from hexane. The yield was 110 mg (18%).

M.p. 162°–163° C. Analysis calc'd for $C_{14}H_{11}ClN_2O_3$: C 57.84, H 3.81, N, 9.64. Found: C, 57.59, H 3.54, N 9.49.

$^1$H NMR (CDCl$_3$) δ8.43 (d, J=1.7 Hz, 1H), 8.11 (s, 1H), 7.86 (s, 1H), 7.38 (d, J=3.5 Hz, 1H), 6.72 (dd, J=1.7, 3.5 Hz, 1H), 4.04 (q, J=7.1 Hz, 2H), 1.35 (t, J=7.1 Hz, 3H).

IR (KBr disc) 1645, 1620, 1535, 1470, 1440 cm$^{-1}$. MS m/z (relative percent) 292 (8), 290 (27), 224 (32), 222 (100), 209 (8), 207 (27), 196 (28), 194 (86), 95 (70).

EXAMPLE 55

5-Chloro-1-ethyl-7-azaoxindole-3-N-(4-fluorophenyl) carboxamide

The title compound was prepared from 5-chloro-1-ethyl-7-azaoxindole (Example 53D) according to the procedure of Example 53E using 5-chloro-1-ethyl-7-azaoxindole (400 mg, 2.03 mmol), 4-dimethylamino pyridine (537 mg, 4.4 mmol), 4-fluorophenylisocyanate (0.25 mL, 2.2 mmol) and DMF (10 mL). The only deviation from this procedure was that the reaction mixture was poured into ice/water and then acidified to pH 3 using 6N hydrogen chloride solution. The solid product obtained after chromatography was recrystallized from ether/hexane. The yield was 95 mg (15%).

M.p. 155°–157° C. (dec.). Analysis calc'd for $C_{16}H_{13}ClFN_3O_2$: C 57.58, H 3.93, N 12.59. Found: C 57.50, H 3.64, N 12.33.

$^1$H NMR (CDCl$_3$) δ9.42 (br s, 1H), 8.22 (s, 1H), 8.05 (s, 1H), 7.53 (dd, J=5, 7 Hz, 1H), 7.02 (t, J=7 Hz, 1H), 4.43 (s, 1H), 3.90 (q, J=7 Hz, 2H), 1.29 (t, J=7H, 3H). IR (KBr disc) 1725, 1665, 1605, 1580, 1550, 1510, 1470, 1435 cm$^{-1}$. MS m/z (relative percent) 335 (18), 333 (52), 198 (33), 196 (100), 170 (10), 168 (30), 111 (21).

EXAMPLE 56

5-Chloro-1-ethyl-7-azaoxindole-3-N-phenylcarboxamide

The title compound was prepared from 5-chloro-1-ethyl-7-azaoxindole (Example 53D) according to the procedure of Example 55, using 5-chloro-1-ethyl-7-azaoxindole (451 mg, 2.29 mmol), 4-dimethylaminopyridine (607 mg, 4.97 mmol), phenylisocyanate (0.27 mL, 2.48 mmol) and DMF (11 mL). After pouring into water and acidification, the reaction mixture yielded a solid which was collected by filtration. This was triturated with ethyl acetate to provide a white solid (not the desired product). The mother liquors were then concentrated to provide a brown solid which was triturated with cold ethyl acetate. The resulting yellow solid was recrystallized from cyclohexane to provide the title compound as a white solid, 38 mg (5%).

M.p. 157°–158° C. Analysis calc'd for $C_{16}H_{14}ClN_3O_2$: C 60.86, H 4.47, N 13.31. Found: C 60.83, H 4.27, N 13.13.
$^1$H NMR (CDCl$_3$) δ9.43 (br s, 1H), 8.21 (s, 1H), 8.04 (s, 1H), 7.48–7.54 (m, 2H), 7.35–7.24 (m, 2H), 7.15–7.10 (m, 1H), 4.41 (s, 1H), 3.91 (q, J=7.3 Hz, 2H), 1.31 (t, J=7.3 Hz, 3H). IR (KBr disc) 1730, 1660, 1605, 1580, 1550, 1470, 1445 cm$^{-1}$. MS m/z (relative percent) 317 (3), 315 (10), 198 (33), 196 (100), 183 (3), 181 (10), 170 (11), 168 (36), 93 (22), 77 (20).

We claim:
1. A compound of the formula

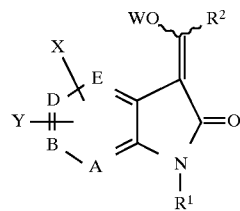

wherein one of A, B, D and E is N and the others are CH; X and Y are independently selected from hydrogen, OR$^3$, hydroxy, (C$_1$–C$_6$) alkyl, CF$_3$, COR$^3$, halogen, COOR$^3$, CONR$^3$R$^3$, CN, NO$_2$, SR$^3$, SOR$^3$, SO$_2$R$^3$ and SO$_2$NR$^3$R$^3$; R$^1$ is (C$_1$–C$_6$) alkyl or CONHR$^4$; R$^2$ is (C$_1$–C$_8$) alkyl, (CH$_2$)$_n$R$^5$ wherein n is 0 or 1, or NHR$^6$; R$^3$ is (C$_1$–C$_6$) alkyl, phenyl, benzyl, allyl or hydrogen, wherein said phenyl and the phenyl moiety of said benzyl may optionally be substituted with one or more substituents independently selected from fluoro, chloro, bromo, iodo, hydroxy, (C$_1$–C$_3$)alkyl, (C$_1$–C$_3$)alkoxy and CF$_3$; R$^4$ is hydrogen, (C$_1$–C$_6$)alkyl, (C$_2$–C$_6$) hydroxyalkyl, (C$_3$–C$_8$) cycloalkyl, COR$^3$ wherein R$^3$ is as defined above, phenyl, substituted phenyl, heteroaryl or substituted heteroaryl, wherein the heteroaryl moiety of each of said heteroaryl and substituted heteroaryl groups is selected from thiophene and furan, and wherein each of said substituted phenyl and substituted heteroaryl groups is substituted with one or two substituents independently selected from fluoro, chloro, bromo, iodo, hydroxy, (C$_1$–C$_3$) alkyl, (C$_1$–C$_3$) alkoxy and CF$_3$; R$^5$ is (C$_3$–C$_8$) cycloalkyl, hydrogen, phenyl, substituted phenyl, heteroaryl and substituted heteroaryl, wherein the heteroaryl moiety of each of said heteroaryl and substituted heteroaryl groups is selected from thiophene and furan, and each of said substituted phenyl and substituted heteroaryl groups is substituted with one or two substituents independently selected from fluoro, chloro, bromo, iodo, hydroxy, (C$_1$–C$_3$) alkyl, (C$_1$–C$_3$) alkoxy and trifluoromethyl; R$^6$ is phenyl, thiophene or furan, wherein said phenyl, thiophene and furan may be optionally substituted with one or more substituents independently selected from fluoro, chloro, bromo, iodo, hydroxy, (C$_1$–C$_6$) alkyl, (C$_1$–C$_3$) alkoxy and trifluoromethyl; and W is hydrogen, (C$_2$–C$_{10}$) alkanoyl, (C$_5$–C$_7$) cycloalkylcarbonyl, (C$_7$–C$_{10}$) phenylalkanoyl, chlorobenzoyl, thenoyl, omega-(C$_2$–C$_4$) alkoxycarbonyl-(C$_3$–C$_5$)alkanoyl, (C$_2$–C$_{10}$) alkoxycarbonyl, phenoxycarbonyl, 1-[(C$_1$–C$_4$) acyloxy]-(C$_2$–C$_4$)alkyl, 1-[(C$_2$–C$_5$)alkoxycarbonyloxy]-(C$_1$–C$_4$)alkyl, (C$_1$–C$_3$)alkylsulfonyl, (C$_1$–C$_3$)alkyl, methylphenylsulfonyl and di-(C$_1$–C$_3$) alkyl phosphonate; with the proviso that (a) when E is nitrogen, then at least one of X and Y is other than hydrogen; (b) when either R$^2$ is NHR$^6$ or R$^1$ is (C$_1$–C$_6$) alkyl, then W is hydrogen;

or a pharmaceutically acceptable salt thereof.

2. A compound according to claim 1, wherein B or E is nitrogen, at least one of X and Y is chloro, R$^2$ is (CH$_2$)R$^5$, n is 0, R$^5$ is unsubstituted heteroaryl, R$^1$ is CONHR$^4$ and R$^4$ is hydrogen or (C$_1$–C$_6$)alkyl.

3. A compound according to claim 1, selected from the group consisting of:
   5-Chloro-3-(2-thenoyl)-4-azaoxindole-1-N-t-butylcarboxamide;
   5-Chloro-3-(2-furoyl)-4-azaoxindole-1-N-t-butylcarboxamide;
   6-Chloro-3-(2-thenoyl)-4-azaoxindole-1-carboxamide;
   5-Chloro-3-(2-thenoyl)-6-azaoxindole-1-N-t-butylcarboxamide;
   5,6-Dichloro-3-(2-thenoyl)-4-azaoxindole-1-N-t-butylcarboxamide;
   5-Chloro-3-(4-methyl-2-thenoyl)-4-azaoxindole-1-N-t-butylcarboxamide;
   5-Chloro-3-(4-chloro-2-thenoyl)-4-azaoxindole-1-N-t-butylcarboxamide;
   5-Chloro-3-(3-furoyl)-4-azaoxindole-1-N-t-butylcarboxamide; and
   5-Chloro-3-(2-thenoyl)-4-azaoxindole-1-N-phenyl carboxamide.

4. A compound according to claim 1, selected from the group consisting of:
   5-Chloro-3-(3-furoyl)-4-azaoxindole-1-N-t-butylcarboxamide;
   5-Chloro-3-(2-thenoyl)-4-azaoxindole-1-N-phenyl carboxamide;
   5-Chloro-3(2-thenoyl)-4-azaoxindole-1-N-t-butylcarboxamide;
   6-Chloro-3-(2-thenoyl)-4-azaoxindole-1-carboxamide;
   5-Chloro-3-(2-thenoyl)-6-azaoxindole-1-N-t-butylcarboxamide;
   3-(2-Thenoyl)-5-azaoxindole-1-N-t-butylcarboxamide;
   6-Fluoro-3-(2-thenoyl)-4-azaoxindole-1-N-t-butylcarboxamide;
   5,6-Dichloro-3-(2-thenoyl)-4-azaoxindole-1-N-t-butylcarboxamide;
   3-(2-Thenoyl)-6-trifluoromethyl-4-azaoxindole-1-N-t-butylcarboxamide;
   3-(2-Furoyl)-6-trifluoromethyl-4-azaoxindole-2-N-t-butyl-carboxamide;
   5-Isopropoxy-3-(2-thenoyl)-4-azaoxindole-1-N-t-butyl-carboxamide;

6-Chloro-3-(2-thenoyl)-4-azaoxindole-1-N-t-butylcarboxamide;
6-Chloro-3-(2-furoyl)-4-azaoxindole-1-N-t-butylcarboxamide;
6-Chloro-3-(3-furoyl)-4-azaoxindole-1-carboxamide;
3-Benzoyl-6-chloro-4-azaoxindole-1-N-t-butylcarboxamide;
6-Chloro-3-(2-furoyl)-4-azaoxindole-1-carboxamide;
5,6-Dichloro-3-(2-thenoyl)-4-azaoxindole-1-carboxamide;
6-Chloro-3-(4-chloro-2-thenoyl)-4-azaoxindole-1-N-t-butylcarboxamide;
6-Chloro-3-(3-furoyl)-4-azaoxindole-1-N-t-butylcarboxamide;
3-Benzoyl-6-chloro-4-azaoxindole-1-carboxamide;
6-Chloro-3-(4-chloro-2-thenoyl)-4-azaoxindole-1-carboxamide;
6-Chloro-3-(4-methyl-2-thenoyl)-4-azaoxindole-1-N-t-butylcarboxamide;
6-Chloro-3-(2-thenoyl)-4-azaoxindole-1-N-phenylcarboxamide;
5-Chloro-3-(2-thenoyl)-4-azaoxindole-1-carboxamide;
5-chloro-3-(2-furoyl)-4-azaoxindole-1-N-t-butylcarboxamide;
5-Chloro-3-(2-furoyl)-4-azaoxindole-1-carboxamide;
5-Chloro-3-(4-chloro-2-thenoyl)-4-azaoxindole-1-N-t-butylcarboxamide;
5-Chloro-3-(2-thenoyl)-4-azaoxindole-1-N-cyclohexylcarboxamide;
5-Chloro-3-(4-chloro-2-thenoyl)-4-azaoxindole-1-carboxamide;
5-Chloro-3-(2-thenoyl)-4-azaoxindole-1-N-(2,4-dichlorophenyl)carboxamide;
5-Chloro-3-(4-methyl-2-thenoyl)-4-azaoxindole-1-N-t-butylcarboxamide;
6-Fluoro-3-(2-thenoyl)-4-azaoxindole-1-carboxamide;
6-Fluoro-3-(4-methyl-2-thenoyl)-4-azaoxindole-1-N-t-butylcarboxamide;
6-Fluoro-3-(4-methyl-2-thenoyl)-4-azaoxindole-1-carboxamide;
3-(2-Thenoyl)-6-azaoxindole-1-N-t-butylcarboxamide;
5-Chloro-3-(2-thenoyl)-6-azaoxindole-1-carboxamide;
3-(2-Thenoyl)-7-azaoxindole-1-N-t-butylcarboxamide;
3-(2-Thenoyl)-6-azaoxindole-1-carboxamide;
3-Phenylacetyl-6-azaoxindole-1-carboxamide;
5-Isopropoxy-3-(2-thenoyl)-4-azaoxindole-1-carboxamide;
5-Phenylthio-3-(2-thenoyl)-6-azaoxindole-1-N-t-butylcarboxamide;
5-Chloro-3-(4-methyl-2-thenoyl)-4-azaoxindole-1-carboxamide;
3-Benzoyl-5-chloro-4-azaoxindole-1-N-t-butylcarboxamide;
5-Chloro-3-(2-thenoyl)-4-azaoxindole-1-N-methylcarboxamide;
5-Chloro-3-(2-thenoyl)-4-azaoxindole-1-N-ethylcarboxamide;
5-Chloro-3-(2-thenoyl)-4-azaoxindole-1-N-isopropylcarboxamide;
3-Benzoyl-5-chloro-4-azaoxindole-1-carboxamide;
5,6-Dichloro-3-(2-furoyl)-4-azaoxindole-1-N-t-butylcarboxamide;
5-Chloro-3-(2-furoyl)-4-azaoxindole-1-N-(1-hydroxy-2-methyl)prop-2-ylcarboxamide;
5-Chloro-1-ethyl-3-(2-thenoyl)-7-azaoxindole;
5-Chloro-1-ethyl-3-(2-furoyl)-7-azaoxindole:
5-Chloro-1-ethyl-7-azaoxindole-3-N-(4-fluorophenyl)carboxamide;
5-Chloro-1-ethyl-7-azaoxindole-3-N-phenylcarboxamide;
3-(4-chloro-2-thenoyl)-5-azaoxindole-1-N-t-butylcarboxamide; and
3-(2-Thenoyl)-5-azaoxindole-1-carboxamide.

5. A pharmaceutical composition for treating one or more conditions in a mammal, selected from the group consisting of asthma, allergy, bronchitis, pulmonary hypertension, pulmonary hypoxia, psoriasis, rheumatoid arthritis, osteoarthritis, inflammatory bowel disease, cardiovascular spasm, acute myocardial infarctions, and autoimmune diseases such as syptemic lupus erythematosis, comprising an amount of a compound according to claim 1 effective in treating one or more of said conditions, and a pharmaceutically acceptable carrier.

6. A method of treating a mammal affected by one or more conditions selected from the group consisting of asthma, allergy, bronchitis, pulmonary hypertension, pulmonary hypoxia, psoriasis, rheumatoid arthritis osteoarthritis, inflammatory bowel disease, cardiovascular spasm, acute myocardial infarctions, and autoimmune diseases such as syptemic lupus erythematosis, comprising administering to said mammal an amount of a compound according to claim 1 effective in treating or preventing one or more of said conditions.

7. A compound of the formula

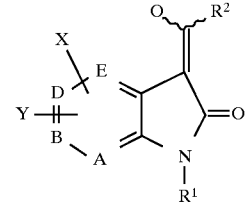

wherein one of A, B, D and E is N and the others are CH; X and Y are independently selected from hydrogen, $(C_1-C_6)$ alkyl, $CF_3$, $COR^3$, halogen, $COOR^3$, $CONR^3R^3$, $CN$, $NO_2$, $SO_2R^3$ and $SO_2NR^3R^3$; $R^1$ is $(C_1-C_6)$alkyl or $CONHR^4$; $R^2$ is $(C_1-C_8)$alkyl or $(CH_2)_nR^5$, wherein n is 0 or 1; $R^3$ is $(C_1-C_6)$ alkyl, phenyl, or hydrogen, wherein said phenyl may optionally be substituted with one or more substituents independently selected from fluoro, chloro, bromo, iodo, hydroxy, $(C_1-C_3)$alkyl, $(C_1-C_3)$alkoxy and $CF_3$; $R^4$ is hydrogen, $(C_1-C_6)$alkyl, $(C_3-C_8)$cycloalkyl, $COR^3$ wherein $R^3$ is as defined above, phenyl, or substituted phenyl, wherein said substituted phenyl is substituted with one or two substituents independently selected from fluoro, chloro, bromo, iodo, hydroxy, $(C_1-C_3)$alkyl, $(C_1-C_3)$alkoxy and $CF_3$; $R^5$ is $(C_3-C_8)$alkyl, hydrogen, phenyl, substituted phenyl, heteroaryl, or substituted heteroaryl, wherein the heteroaryl moiety of each of said heteroaryl and substituted heteroaryl groups is selected from thiophene and furan, and wherein each of said substituted phenyl and substituted heteroaryl groups is substituted with one or two substituents independently selected from fluoro, chloro, bromo, iodo, hydroxy, $(C_1-C_3)$alkyl, $(C_1-C_3)$alkoxy and $CF_3$; with the proviso that when E is nitrogen, then at least one of X and Y is other than hydrogen;

or a pharmaceutically acceptable salt thereof.

8. A compound according to claim 7, wherein B or E is nitrogen, at least one of X and Y is chloro, $R^2$ is $(CH_2)_nR^5$, n is 0, $R^5$ is unsubstituted heteroaryl, $R^1$ is $CONHR^4$, and $R^4$ is hydrogen or $(C_1-C_6)$alkyl.

9. A compound according to claim 7, selected from the group consisting of:

5-Chloro-3-(2-thenoyl)-4-azaoxindole-1-N-t-butylcarboxamide;
5-Chloro-3-(2-furoyl)-4-azaoxindole-1-N-t-butylcarboxamide;
6-Chloro-3-(2-thenoyl)-4-azaoxindole-1-carboxamide;
5-Chloro-3-(2-thenoyl)-6-azaoxindole-1-N-t-butylcarboxamide;
5,6-Dichloro-3-(2-thenoyl)-4-azaoxindole-1-N-t-butylcarboxamide;
5-Chloro-3-(4-methyl-2-thenoyl)-4-azaoxindole-1-N-t-butylcarboxamide;
5-Chloro-3-(4-chloro-2-thenoyl)-4-azaoxindole-1-N-t-butylcarboxamide;
5-Chloro-3-(3-furoyl)-4-azaoxindole-1-N-t-butylcarboxamide; and
5-Chloro-3-(2-thenoyl)-4-azaoxindole-1-N-phenyl carboxamide.

10. A compound according to claim 7, selected from the group consisting of:

5-Chloro-3-(3-furoyl)-4-azaoxindole-1-N-t-butylcarboxamide;
5-Chloro-3-(2-thenoyl)-4-azaoxindole-1-N-phenylcarboxamide;
5-Chloro-3-(2-thenoyl)-4-azaoxindole-1-N-t-butylcarboxamide;
6-Chloro-3-(2-thenoyl)-4-azaoxindole-1-carboxamide;
5-Chloro-3-(2-thenoyl)-6-azaoxindole-1-N-t-butylcarboxamide;
3-(2-Thenoyl)-5-azaoxindole-1-N-t-butyl-carboxamide;
6-Fluoro-3-(2-thenoyl)-4-azaoxindole-1-N-t-butylcarboxamide;
5,6-Dichloro-3-(2-thenoyl)-4-azaoxindole-1-N-t-butylcarboxamide;
3-(2-Thenoyl)-6-trifluoromethyl-4-azaoxindole-1-N-t-butylcarboxamide;
3-(2-Furoyl)-6-trifluoromethyl-4-azaoxindole-2-N-t-butyl-carboxamide;
6-Chloro-3-(2-thenoyl)-4-azaoxindole-1-N-t-butylcarboxamide;
6-Chloro-3-(2-furoyl)-4-azaoxindole-1-N-t-butylcarboxamide;
6-Chloro-3-(3-furoyl)-4-azaoxindole-1-carboxamide;
3-Benzoyl-6-chloro-4-azaoxindole-1-N-t-butylcarboxamide;
6-Chloro-3-(2-furoyl)-4-azaoxindole-1-carboxamide;
5,6-Dichloro-3-(2-thenoyl)-4-azaoxindole-1-carboxamide;
6-Chloro-3-(4-chloro-2-thenoyl)-4-azaoxindole-1-N-t-butylcarboxamide;
6-Chloro-3-(3-furoyl)-4-azaoxindole-1-N-t-butylcarboxamide;
3-Benzoyl-6-chloro-4-azaoxindole-1-carboxamide;
6-Chloro-3-(4-chloro-2-thenoyl)-4-azaoxindole-1-carboxamide;
6-Chloro-3-(4-methyl-2-thenoyl)-4-azaoxindole-1-N-t-butylcarboxamide;
6-Chloro-3-(2-thenoyl)-4-azaoxindole-1-N-phenylcarboxamide;
5-Chloro-3-(2-thenoyl)-4-azaoxindole-1-carboxamide;
5-Chloro-3-(2-furoyl)-4-azaoxindole-1-N-t-butylcarboxamide;
5-Chloro-3-(2-furoyl)-4-azaoxindole-1-carboxamide;
5-Chloro-3-(4-chloro-2-thenoyl)-4-azaoxindole-1-N-t-butylcarboxamide;
5-Chloro-3-(2-thenoyl)-4-azaoxindole-1-N-cyclohexylcarboxamide;
5-Chloro-3-(4-chloro-2-thenoyl)-4-azaoxindole-1-N-t-carboxamide;
5-Chloro-3-(2-thenoyl)-4-azaoxindole-1-N-(2,4-dichlorophenyl)carboxamide;
5-Chloro-3-(4-methyl-2-thenoyl)-4-azaoxindole-1-N-t-butylcarboxamide;
6-Fluoro-3-(2-thenoyl)-4-azaoxindole-1-carboxamide;
6-Fluoro-3-(4-methyl-2-thenoyl)-4-azaoxindole-1-N-t-butylcarboxamide;
6-Fluoro-3-(4-methyl-2-thenoyl)-4-azaoxindole-1-carboxamide;
3-(2-Thenoyl)-6-azaoxindole-1-N-t-butylcarboxamide;
5-Chloro-3-(2-thenoyl)-6-azaoxindole-1-carboxamide;
3-(2-Thenoyl)-7-azaoxindole-1-N-t-butylcarboxamide;
3-(2-Thenoyl)-6-azaoxindole-1-carboxamide;
3-Phenylacetyl-6-azaoxindole-1-carboxamide;
5-Chloro-3-(4-methyl-2-thenoyl)-4-azaoxindole-1-carboxamide;
3-Benzoyl-5-chloro-4-azaoxindole-1-N-t-butylcarboxamide;
5-Chloro-3-(2-thenoyl)-4-azaoxindole-1-N-methylcarboxamide;
5-Chloro-3-(2-thenoyl)-4-azaoxindole-1-N-ethylcarboxamide;
5-Chloro-3-(2-thenoyl)-4-azaoxindole-1-N-isopropylcarboxamide;
3-Benzoyl-5-chloro-4-azaoxindole-1-carboxamide;
5,6-Dichloro-3-(2-furoyl)-4-azaoxindole-1-N-t-butylcarboxamide;
5-Chloro-1-ethyl-3-(2-thenoyl)-7-azaoxindole;
5-Chloro-1-ethyl-3-(2-furoyl)-7-azaoxindole;
5-Chloro-1-ethyl-7-azaoxindole-3-N-phenylcarboxamide;
3-(4-Chloro-2-thenoyl)-5-azaoxindole-1-N-t-butylcarboxamide; and
3-(2-Thenoyl)-5-azaoxindole-1-carboxamide.

11. A pharmaceutical composition for treating one or more conditions in a mammal, selected from the group consisting of asthma, allergy, bronchitis, pulmonary hypertension, pulmonary hypoxia, psoriasis, rheumatoid arthritis, osteoarthritis, inflammatory bowel disease, cardiovascular spasm, acute myocardial infarctions, and autoimmune diseases such as systemic lupus erythematosus, comprising an amount of a compound according to claim 7 effective in treating one or more of said conditions, and a pharmaceutically acceptable carrier.

12. A method of treating a mammal affected by one or more conditions selected from the group consisting of asthma, allergy, bronchitis, pulmonary hypertension, pulmonary hypoxia, psoriasis, rheumatoid arthritis osteoarthritis, inflammatory bowel disease, cardiovascular spasm, acute myocardial infarctions, and autoimmune diseases such as systemic lupus erythematosus, comprising administering to said mammal an amount of a compound according to claim 7 effective in treating or preventing one or more of said conditions.

* * * * *